US012485233B2

(12) United States Patent
Sher et al.

(10) Patent No.: US 12,485,233 B2
(45) Date of Patent: Dec. 2, 2025

(54) DEVICE FOR INJECTING A SUBSTANCE INTO AN INTERLAYER OF A BODY TISSUE OR ORGAN

(71) Applicant: Everads Therapy Ltd., Tel Aviv (IL)

(72) Inventors: Ifat Sher, Shoham (IL); Ygal Rotenstreich, Kfar Bilu (IL); Gad Lewkonya, Neve-Mivtach (IL); David Daily, Herzliya (IL); Lior Raday, Bror Hayil (IL); Hagay Drori, Tel Aviv (IL)

(73) Assignee: EVERADS THERAPY LTD., Tel Aviv (IL)

( * ) Notice: Subject to any disclaimer, the term of this patent is extended or adjusted under 35 U.S.C. 154(b) by 1213 days.

(21) Appl. No.: 17/048,615

(22) PCT Filed: Apr. 18, 2019

(86) PCT No.: PCT/IL2019/050451
§ 371 (c)(1),
(2) Date: Oct. 19, 2020

(87) PCT Pub. No.: WO2019/202603
PCT Pub. Date: Oct. 24, 2019

(65) Prior Publication Data

US 2021/0236743 A1 Aug. 5, 2021

Related U.S. Application Data

(60) Provisional application No. 62/659,831, filed on Apr. 19, 2018.

(51) Int. Cl.
*A61M 5/32* (2006.01)
*A61M 25/02* (2006.01)

(52) U.S. Cl.
CPC .......... *A61M 5/3286* (2013.01); *A61M 25/02* (2013.01); *A61M 2025/028* (2013.01);
(Continued)

(58) Field of Classification Search
CPC ................ A61M 5/3286; A61M 25/02; A61M 2025/028; A61M 2025/0286;
(Continued)

(56) References Cited

U.S. PATENT DOCUMENTS 5,013,304 A * 5/1991 Russell ............. A61M 25/0631 604/167.03
5,540,662 A 7/1996 Nicholson
6,544,239 B2 4/2003 Kinsey et al.
6,629,956 B1 10/2003 Polidoro
2007/0027429 A1 * 2/2007 Kuracina ......... A61B 5/150389 604/116
2009/0076435 A1 * 3/2009 Melsheimer ........ A61M 1/3655 604/6.16
(Continued)

FOREIGN PATENT DOCUMENTS

WO 2016/196841 12/2016

OTHER PUBLICATIONS

PCT Search Report and Written Opinion PCT/IL2019/050451, Aug. 1, 2019.

*Primary Examiner* — Kevin C Sirmons
*Assistant Examiner* — Alexandra Lalonde
(74) *Attorney, Agent, or Firm* — Dekel Patent Ltd.; David Klein

(57) ABSTRACT

Provided is a device for injection into an interlayer of an organ of a subject. The device includes a needle having a size transitional portion terminating in a sharp needle distal tip. The device also includes an elongated tissue separator that is shiftable in the needle lumen. An actuator shifts the tissue separator in the needle lumen between a first position, in which the separator distal tip is fixedly positioned proximally to the needle distal tip, and a second position in which the separator distal tip is fixedly positioned a predetermined distance distally from the needle distal tip.

19 Claims, 20 Drawing Sheets

(52) U.S. Cl.
CPC ............... *A61M 2202/0007* (2013.01); *A61M 2210/0612* (2013.01)

(58) Field of Classification Search
CPC .. A61M 2005/3104; A61M 2210/0612; A61M 5/46; A61M 5/427; A61M 2202/0007; A61M 5/322; A61M 5/32; A61M 5/321; A61M 5/3295; A61M 5/3297; A61M 2005/322; A61M 25/0606; A61M 25/0014; A61M 25/0643; A61M 25/0068; A61M 2005/3227; A61M 2005/3228; A61F 9/0008; A61F 9/0017; A61F 9/008; A61F 9/0026; A61F 2009/0052; A61F 2/1662; A61F 9/00736; A61F 9/00754; A61B 5/150389
USPC .......................................................... 604/272
See application file for complete search history.

(56) References Cited

U.S. PATENT DOCUMENTS

| | | | | |
|---|---|---|---|---|
| 2010/0016801 | A1* | 1/2010 | Rosenberg ............ | A61M 25/02 604/174 |
| 2013/0103145 | A1* | 4/2013 | John ..................... | A61F 9/0017 351/219 |
| 2015/0157787 | A1* | 6/2015 | Cully ...................... | A61M 5/46 604/117 |
| 2015/0351959 | A1* | 12/2015 | Clem .................... | A61F 9/0026 604/116 |
| 2016/0143776 | A1* | 5/2016 | Rotenstreich ......... | A61F 9/0017 604/21 |
| 2016/0354244 | A1 | 12/2016 | Horvath et al. | |
| 2016/0367766 | A1* | 12/2016 | Baker ................. | A61M 5/3287 |
| 2017/0157336 | A1 | 6/2017 | Olson et al. | |
| 2017/0360605 | A1* | 12/2017 | Oberkircher .......... | A61F 9/0017 |
| 2020/0069469 | A1 | 3/2020 | Horvath | |

* cited by examiner

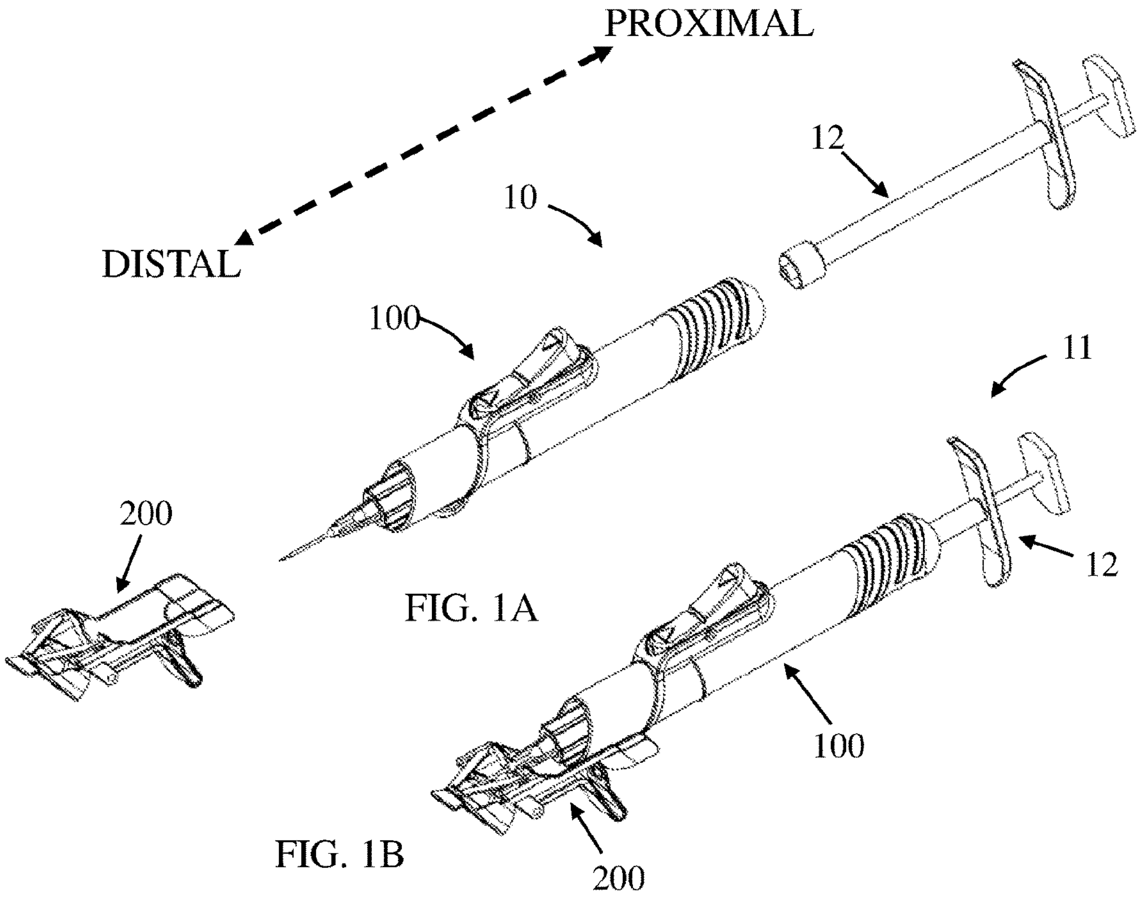
FIG. 1A
FIG. 1B
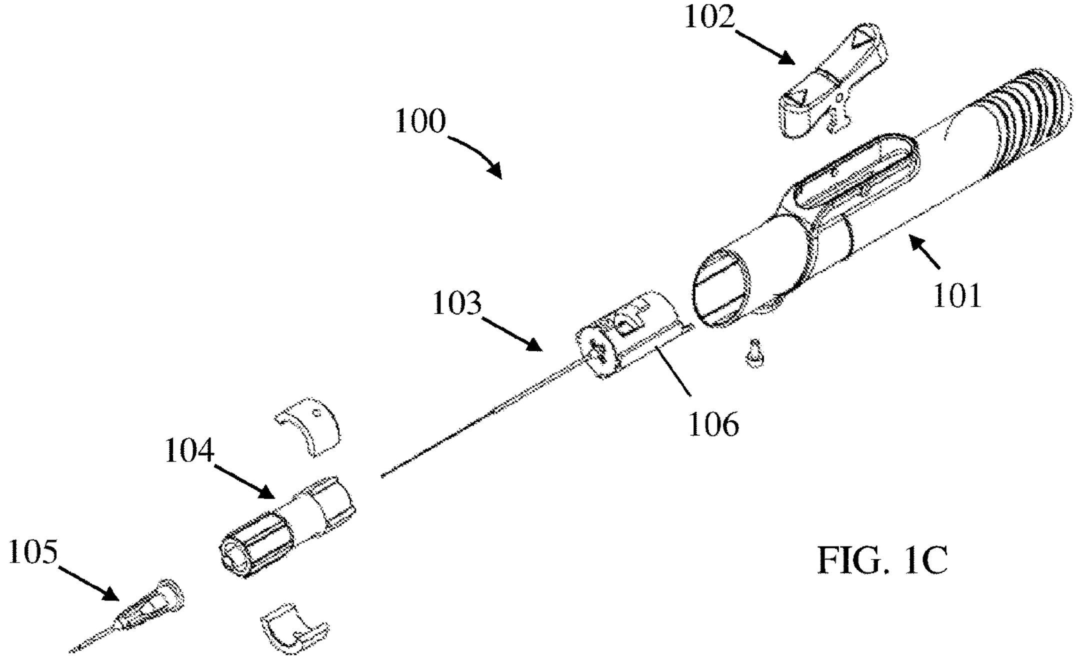
FIG. 1C

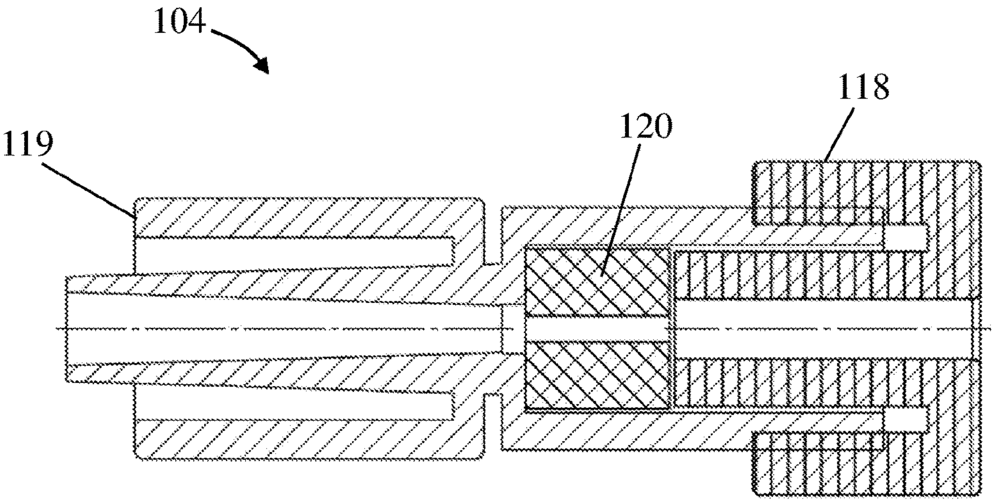
FIG. 4
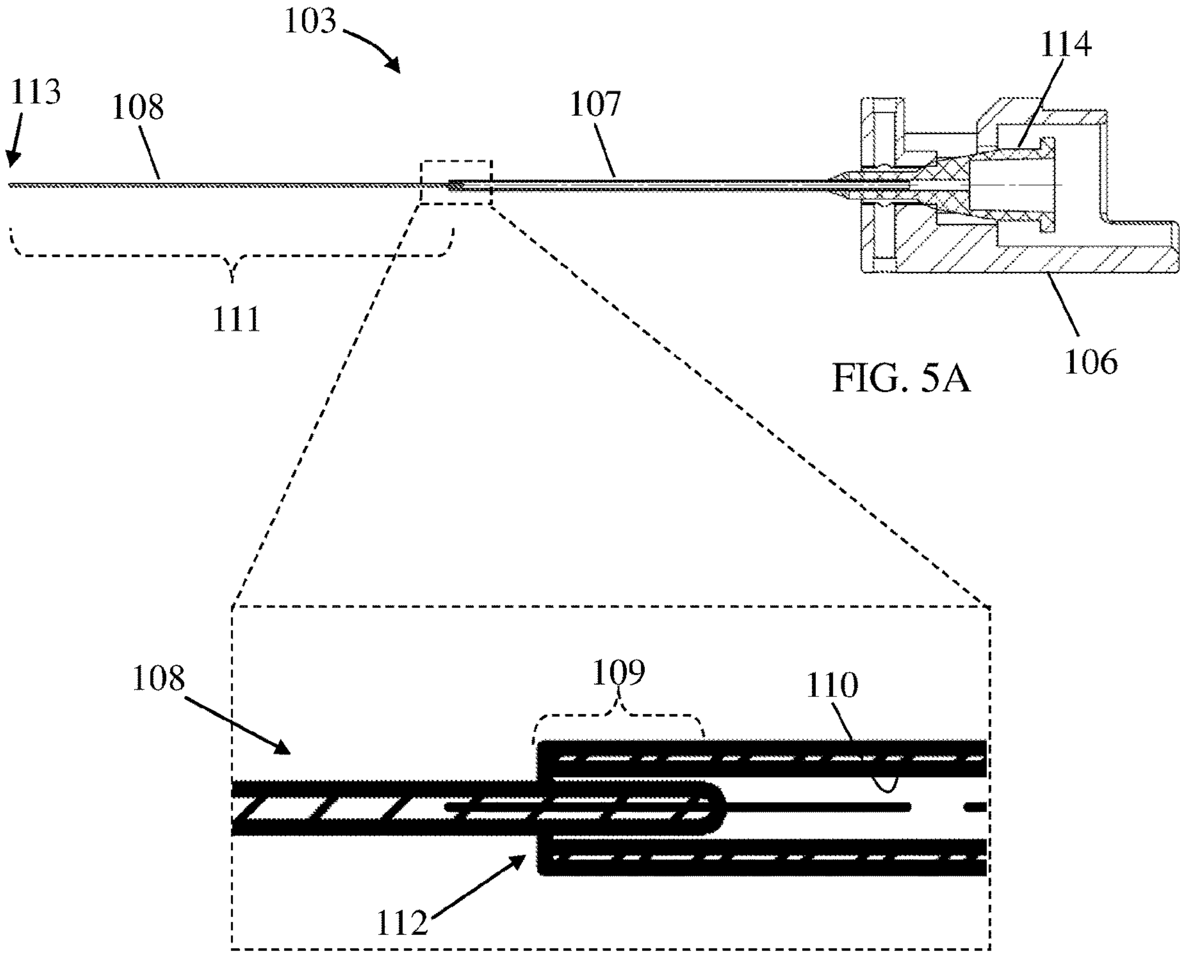
FIG. 5A
FIG. 5B

DEVICE FOR INJECTING A SUBSTANCE INTO AN INTERLAYER OF A BODY TISSUE OR ORGAN

CROSS REFERENCE TO RELATED APPLICATIONS

This application claims priority to provisional application 62/659,831, filed 19 Apr. 2018, and is a 371 application of PCT/IL2019/050451, filed 18 Apr. 2019.

FIELD OF THE INVENTION

The present invention relates to devices and methods for injecting one or more substances into a body tissue such as an eye.

BACKGROUND OF THE INVENTION

Posterior segment ocular diseases are the leading causes of irreparable visual impairment in industrialized countries. These include, among other, age-related macular degeneration (AMD), diabetic retinopathy (DR) and retinitis pigmentosa (RP). There are currently estimated nearly 200 million known patients with AMD and over 100 million known patients with DR worldwide.

Current treatments of these diseases and development and evaluation of new advanced treatments are limited by the difficulty in delivering effective doses of drugs, gene therapy and cellular therapy substances to the target posterior tissues, such as posterior portions of the retina, the retinal pigmented epithelium (RPE) and the choroid, due to tissue barriers (such as the cornea, conjunctiva, blood aqueous barrier, and blood-retinal barrier) which limit the access of drugs delivered to posterior regions.

Therefore, there is still a need for new devices and methods for treating diseases affecting the back of the eye based on new effective and safe delivery strategies to circumvent the ocular barriers.

SUMMARY OF THE INVENTION

In one of its aspects, the present invention provides a device for injection into an interlayer of an organ of a subject, comprising:

a needle comprising a needle lumen extending between a needle proximal end and a needle distal end, said needle distal end including a size transitional portion terminating in a sharp needle distal tip;

an elongated tissue separator having a separator distal tip, at least a portion of said tissue separator being shiftable in the needle lumen; and an actuator configured to shift said tissue separator in said needle lumen between a first position, wherein said separator distal tip is fixedly positioned proximally to said needle distal tip, and a second position, wherein said separator distal tip is fixedly positioned a first predetermined distance distally from said needle distal tip.

When said separator distal tip is in said first position, said separator distal tip may protrude from a laterally uncovered section of said size transitional portion.

The device of the invention may be configured for injecting any one or more of a liquid, a gel, a semi-solid, a solid object, a low viscosity fluid, a high viscosity fluid, a suspension, a cell suspension, an emulsion, a solution, a nanotherapy, microspheres, and insert and an implant.

The device may further comprise a cannula fluidly connectable between a syringe and said needle lumen, so that a fluid injected from said syringe is directly flowable to said needle distal tip via said cannula and said needle lumen.

The tissue separator may have any one or more of the following features:

a. said tissue separator includes said cannula and an elongated probe comprising a probe fixed portion connected to an inner cannula wall of said cannula and a probe protruding portion extending distally from a cannula distal end of said cannula and terminating in said separator distal tip;

b. said tissue separator is configured to allow flow of a fluid from said cannula to said needle lumen around said probe fixed portion;

c. the cannula is provided with a seal configured to allow sliding of said tissue separator therealong;

d. the cannula is provided with a seal configured to allow sliding of said tissue separator therealong and said cannula distal end is positioned within, or distally to, said seal in each of said preset fixed positions. Said syringe may be connectable to a separator hub of said separator.

The device may be adapted for injection into an eye.

The device may further comprise an external stopper provided externally to said needle and configured to prevent penetration of said needle distal tip in the organ beyond a third predetermined length. The external stopper may have any one or more of the following features:

a. said external stopper is a tube extending along said needle with a stopper distal end thereof located proximally to said needle distal tip by said third predetermined distance; and b. said external stopper is a tube extending along said needle with a stopper distal end thereof located proximally to said needle distal tip by said third predetermined distance and said stopper distal end is fixedly positioned, or selectively shiftable along said needle, proximally to said size transitional portion.

The actuator may comprise a switch, the switch being switchable between two or more switch modes for shifting the actuator between fixed positions of the actuator.

The device may further comprise an organ docking device for fixating a target tissue portion of the organ and directing needle penetration into the target tissue portion, the organ docking device comprising:

an organ docking device body comprising an organ contact surface, configured to conform to a surface of the target tissue portion, and a guide configured to guide the needle in a penetration path through said contact surface;

an anchoring member configured to anchor the organ docking device to said target tissue portion; and an anchoring actuator configured to shift said anchoring member between a withdrawn position, wherein said anchoring member is prevented from physically interacting with the target tissue portion when in contact with said organ contact surface, and an anchoring position, wherein said anchoring member anchors to said tissue target portion so as to generate counteracting forces between said organ docking device body and the organ during penetration into the target tissue portion with said needle along said predetermined needle penetration path.

The guide may be tiltable relative to the organ docking device.

The anchoring member may have any one or more of the following properties:

a. said anchoring member comprises at least one anchor connected to said organ docking device body each anchor being provided with a sharp anchor tip for penetrating into said target tissue portion;
b. when the anchoring member is in said withdrawn position, each anchor tip is positioned proximally to said organ contact surface, and when the anchoring member is in said anchoring position, said anchor tip is positioned distally to said organ contact surface for anchoring to the target tissue portion; and
c. when the anchoring member is in said anchoring position, said at least one anchor is directed from a peripheral point towards an opposing peripheral point, around said contact organ surface.

The device may further comprise a tissue pressing member configured for pressing against said target tissue portion when in contact with said organ contact surface.

The anchoring member may include a first anchor and a second anchor.

The needle penetration path may pass between said first and second anchors.

One of said at least one anchor may include an anchor size transitional portion ending with said anchor distal tip and a slender restrictor with a blunt restrictor tip thereof fixedly positioned between ends of said anchor size transitional portion and is protruding from a laterally uncovered section of said size transitional portion.

The anchoring actuator may comprise an anchoring trigger configured to cause at least one anchor to shift between said withdrawn position and said anchoring position.

The organ contact surface may be configured to conform to a conjunctiva tissue or/and a sclera tissue of an eyeball.

The soft tissue pressing member may be configured to press a conjunctiva tissue to a sclera tissue of an eyeball.

The guide may be formed as an elongated concave surface fixedly inclined to said organ contact surface.

The docking device body may include a penetration restricting element configured to prevent distal advancement of said apparatus along said guide beyond a predetermined maximal travel length.

The organ docking device body may include a magnet configured for creating a snug fit between said guide and an apparatus surrounding the needle.

The device may further comprise a reservoir, such as a syringe.

In another of its aspects, the present invention provides a method for injection of a substance or object into an interlayer region in an eye of a subject, the method comprising:

a. Providing a device for injection into an interlayer of an organ of a subject, the device comprising:
a needle comprising a needle lumen extending between a needle proximal end and a needle distal end, said needle distal end including a size transitional portion terminating in a sharp needle distal tip;
an elongated tissue separator having a separator distal tip, at least a portion of said tissue separator being shiftable in the needle lumen; and
an actuator configured to shift said tissue separator in said needle lumen between a first position, wherein said separator distal tip is fixedly positioned proximally to said needle distal tip, and a second position, wherein said separator distal tip is fixedly positioned a first predetermined distance distally from said needle distal tip;
b. positioning said separator distal tip at the first position between ends of said size transitional portion,
c. positioning said separator distal tip at a first predetermined distance proximally to said needle distal tip, the separator distal tip protruding from the size transitional portion;
d. penetrating outer surface of the organ at a penetration point into the organ using said needle distal tip until contacting an organ outer surface layer with said separator distal tip, wherein said first predetermined length is shorter than a thickness of said outer surface layer adjacent to said penetration point, and
e. injecting said substance or object into the interlayer.

The method of the invention may further comprise using said actuator to shift said tissue separator longitudinally in said needle lumen such that said separator distal tip is repositioned to a distal-most position, wherein said separator distal tip is located a second predetermined length distally to said needle distal tip, thereby advancing in said outer surface layer and penetrating through said outer surface layer into the interlayer of the organ and forming a passage in said interlayer with said separator distal tip.

All technical or/and scientific words, terms, or/and phrases, used herein have the same or similar meaning as commonly understood by one of ordinary skill in the art to which the invention pertains, unless otherwise specifically defined or stated herein. Exemplary embodiments of methods (steps, procedures), apparatuses (devices, systems, components thereof), equipment, and materials, illustratively described herein are exemplary and illustrative only and are not intended to be necessarily limiting. Although methods, apparatuses, equipment, and materials, equivalent or similar to those described herein can be used in practicing or/and testing embodiments of the invention, exemplary methods, apparatuses, equipment, and materials, are illustratively described below. In case of conflict, the patent specification, including definitions, will control.

BRIEF DESCRIPTION OF THE DRAWINGS

Some embodiments of the present invention are herein described, by way of example only, with reference to the accompanying drawings. With specific reference now to the drawings in detail, it is stressed that the particulars shown are by way of example and for purposes of illustrative description of some embodiments of the present invention. In this regard, the description taken together with the accompanying drawings make apparent to those skilled in the art how some embodiments of the present invention may be practiced.

In the drawings:

FIGS. 1A-1B respectively illustrate isometric views of an exemplary kit for assembling an exemplary system, and the exemplary system shown fully assembled, that is configured for facilitating and performing injections to an interlayer region in eye of a subject, according to some embodiments of the invention;

FIG. 1C illustrates an isometric view of elements forming an organ affecting device for facilitating fluid injection to an interlayer region in an eye of a subject, according to some embodiments of the invention;

FIG. 4 illustrates a side cut view of an exemplary sealed connector member, according to some embodiments of the invention;

FIGS. 5A-5B respectively illustrate a side cut view and a magnified portion of an exemplary tissue separator, according to some embodiments of the invention;

FIGS. 12A-120 illustrate views of the exemplary system shown in FIG. 1B in different configurations representing exemplary steps in a method for fixating a sclera portion, directing needle penetration into the sclera portion, and facilitating fluid injection to an interlayer region in an eye of a subject, according to some embodiments of the invention;

DESCRIPTION OF SPECIFIC EMBODIMENTS OF THE INVENTION

Figure 2A:
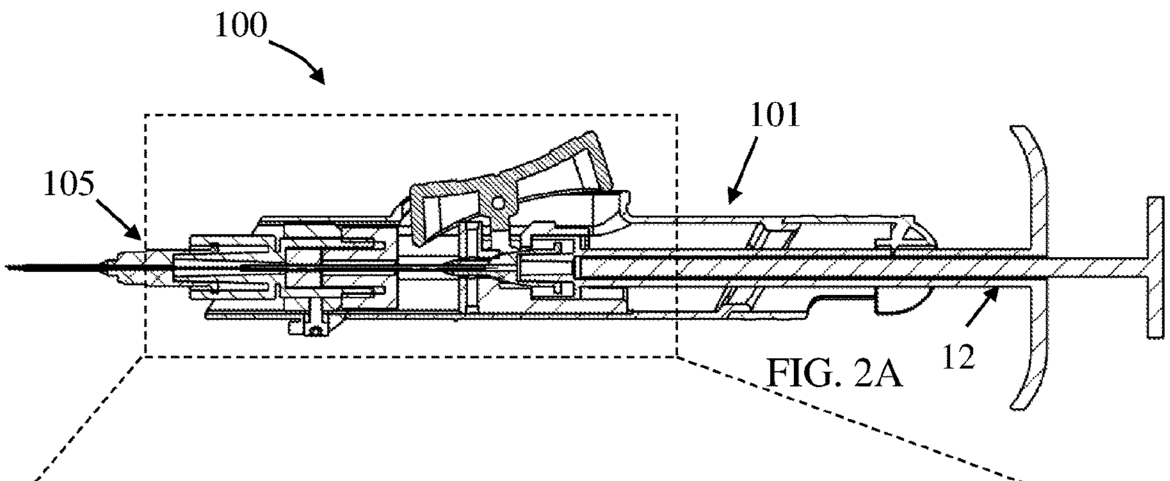
FIGS. 2A-2B respectively illustrate a side cut view and a magnified portion of the exemplary device shown in FIG. 1C assembled with an exemplary syringe, according to some embodiments of the invention.

The present invention, in some embodiments thereof, relates to devices and methods for treating an eye of a subject, and more particularly, but not exclusively, to devices and methods for delivering medications to an interlayer region of the eye.

According to an aspect of some embodiments of the present invention, there is provided a device, or a number of interconnected devices, configured for introduction of one or more substances, such as a fluid, semi solid or semi-fluid substance, or an object, such as an implant, into an interlayer region in an organ of a subject. In some embodiments, such means (devices) are applicable for forming a route (optionally in a form of a punctured or broached passage), having a predetermined or/and user selected features of spatial direction, contour and dimensions, and afterwards for delivering the substance or object into and along this route, and from the route to dispersion across most or all of the interlayer region. Such devices can be provided to a user disassembled in a form of a kit, readily assembled in a form of a system, or provided separately as distinct devices.

The subject may be a human or animal patient. The organ may be an eye of the subject, as may be considered particularly relevant in some of the exemplary embodiments described herein, although at least some exemplary embodiments of the present invention may be considered relevant for treating or/and affecting other organs or tissues (by way of injecting medicament therein, or facilitating injection in preferred manner, for example).

Reference is made to FIGS. 1A-1C. FIG. 1A illustrates an exemplary kit 10 for assembling an exemplary system 11, which is configured for facilitating and performing injections to an interlayer region in an organ (e.g., eye) of a subject. FIG. 1B illustrates system 11 fully assembled. Kit 10 or system 11 includes a fluid reservoir, such as a syringe 12, an organ affecting device 100, and an organ docking device 200.As will be further described below, organ docking device 200 is configured for fixating a target tissue portion (e.g., target portion of a sclera) of an organ (e.g., an eye of a subject) and for directing needle penetration into the target tissue portion, such as by physically confining a path for sliding thereon to organ affecting device 100 in a chosen spatial direction relative to the target tissue portion.

Optionally, organ affecting device 100 is configured for facilitating low to high-volume fluid dispersions in an organ's interlayer region, by creating, prior to injection, a directional spaced passage into and through the outer most or anterior organ layer (e.g., the sclera optionally with the conjunctiva) and an interlayer region (e.g., within choroid layers, or/and between choroid and retina of the eye), in an accurate anatomical location, chosen alignment, and predefined dimensions. This artificial passage is configured for effectively containing, channeling and dispersing fluids therefrom to distant and/or large areas throughout the interlayer region of the organ. In some embodiments, the passage is oriented at a shallow angle (e.g., 0° to) 30°, or substantially tangential, to the target tissue portion and/or to the interlayer region adjacent to point of entry of the needle into the target tissue portion.

FIG. 1C illustrates elements forming organ affecting device 100, which include an actuator 101, a switch 102, a tissue separator 103, a sealed connector member 104 and a needle 105. Needle 105 is configured to penetrate into and/or through a target portion of an outer layer of the organ, such as the sclera of an eye (optionally including also the conjunctiva), tissue separator 103 is configured for passing with distal tip thereof via lumen of needle 105 and is selectively positionable at different fixed positions aimed in accordance with different functions, including at least one of: (i) forming a directional spaced passage, by piercing into and separating (spacing-apart) adjacent layers in an interlayer region portion, (ii) assist in restricting penetration length of needle 105 in the target tissue portion, and (iii) channeling a fluid from syringe 12 into lumen of needle 105.Sealed connector member 104 facilitates fluid tight connection between tissue separator 103 at one end, and needle 105 at an opposing end.

Figure 7:
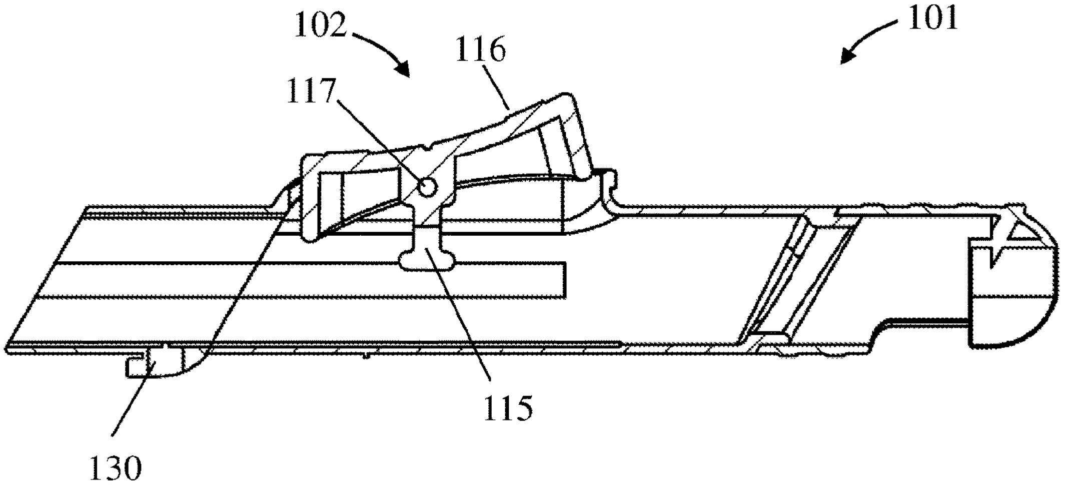
FIG. 7 illustrates a side cut view of an exemplary actuator, according to some embodiments of the invention.

Actuator 101 (shown separately in FIG. 7) forms the handheld body of organ affecting device 100 and configured for housing area of connection of syringe 12 with tissue separator 103. It is equipped with switch 102 for shifting distal tip of tissue separator 103 between preset fixed positions. Switch 102 may be a toggle type switch as illustrated, or it may be of any other type, such as a push button, a revolving knob, or a slide switch, configured with at least two (optionally three) switch positions. Actuator 101 also includes an aligning element 130 configured for fastening into a mating recess region in docking device 200 for facilitating alignment and predetermined travel length along a directing surface of docking device 200.

Figure 2B:
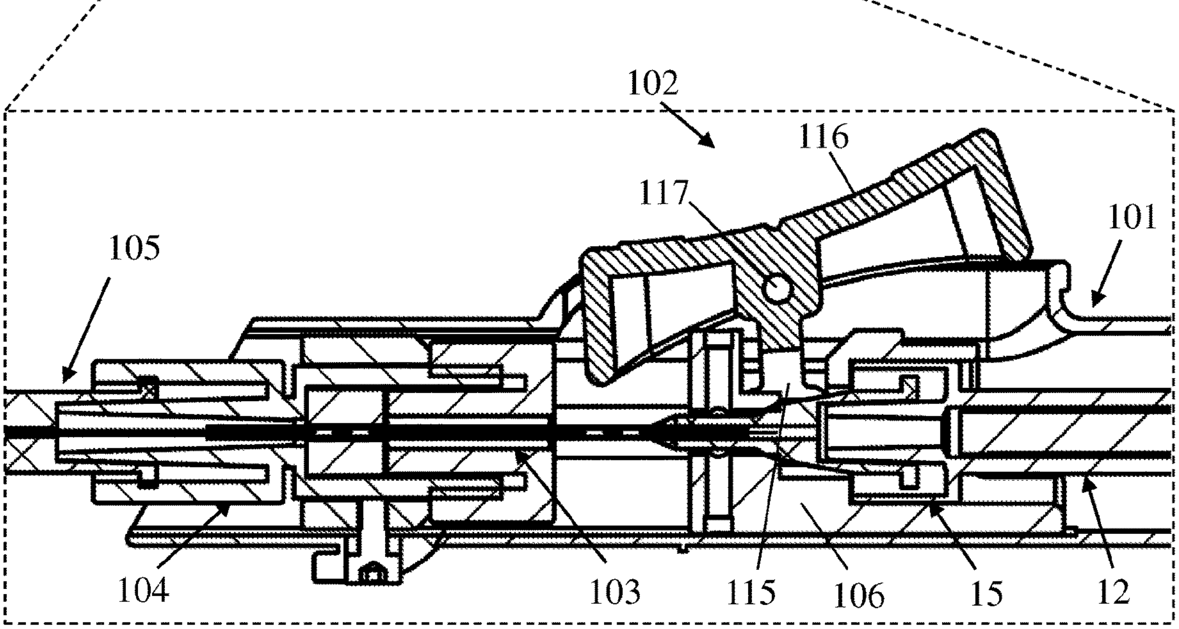
Figure 3:
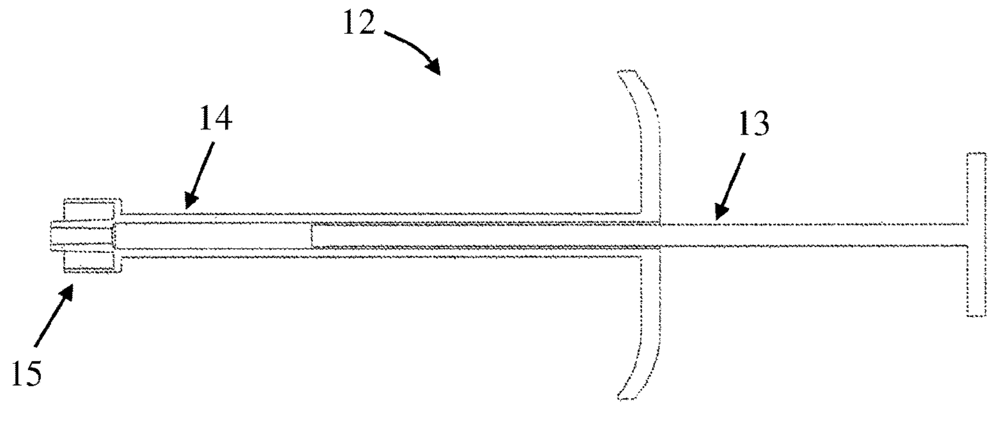
FIG. 3 illustrates a side cut view of an exemplary syringe, according to some embodiments of the invention.

FIGS. 2A-2B respectively illustrate a side cut view and a magnified portion of device 100 assembled with syringe 12.Syringe 12 (shown separately in FIG. 3) includes a piston 13, a barrel14 in which piston 13 slides, and a syringe connector 15. Syringe connector 15 is configured for connecting with device 100 in a dedicated hollow of actuator 101, to a separator hub 106 of tissue separator 103, which may be equipped with a Luer connection 114 or other type of leak-free connector. Tissue separator 103 (shown separately in FIG. 5A-5B) also includes a cannula 107 connecting between separator hub 106 and an elongated probe 108. Probe 108 has a probe fixed portion 109 fixedly connected to an inner cannula wall 110 of cannula 107, and a probe protruding portion 111 which extends distally from a cannula distal end 112 of cannula 107 and ending with a separator distal tip 113. This way of connection facilitates fluid flow from cannula 107 to pass across probe fixed portion 109 towards needle 105. Probe protruding portion 111 has length sufficient to facilitate the preset fixed positions of separator distal tip 113 relative to needle 105. In other embodiments, and as will be described below, a drug reservoir (optionally in a form of a syringe or including a piston) may be provided as an integral part of the tissue affecting device, thus eliminating the need for connectors and hub, which are required for assembling parts but possess significant space and design limitations in the overall design.

Switch 102 engages with separator hub 106 via a switch arm 115 that is connected to a switch button 116 across a switch pivot connection 117, such that moving switch button 116 about switch pivot connection 117 results in shifting tissue separator 103 by pushing it between preset fixed positions via switch arm 115.

Sealed connector member 104 (shown separately in FIG. 4) includes a separator port 118, configured for accommodating length and diameter of cannula 107 therethrough, a needle connector 119 (optionally in a form of a male Luer connection, as shown), configured for leak-free connecting with needle 105, and a seal 120 configured for sealing around cannula 107 while allowing cannula 107 slide therein without compromising sealing properties.

Figure 6A:
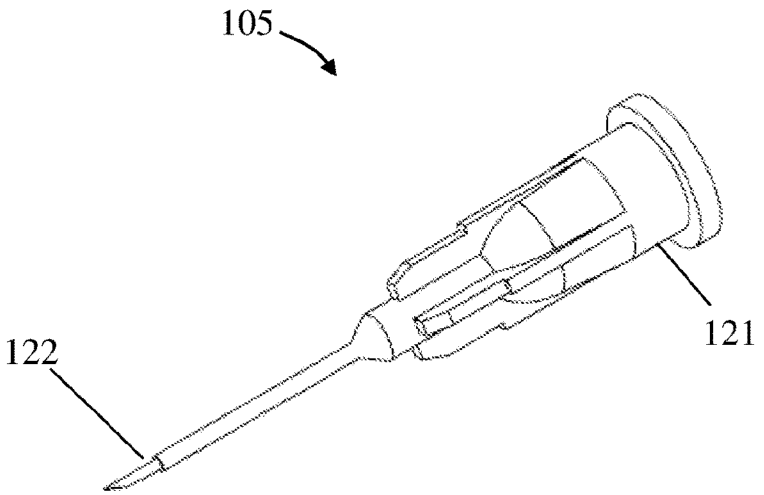
FIGS. 6A-6B respectively illustrate an isometric view and a side cut view of an exemplary needle, according to some embodiments of the invention.
Figure 6B:
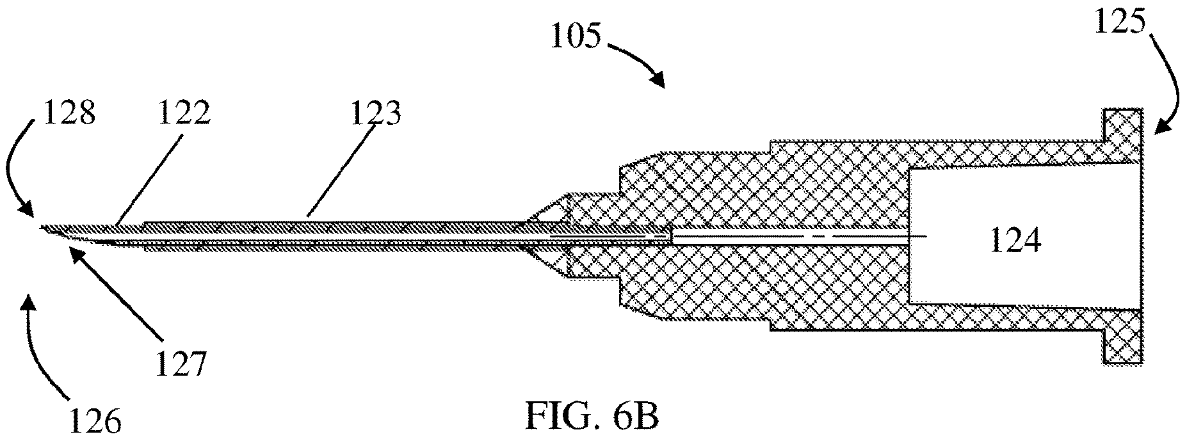

Needle 105 (shown separately in FIGS. 6A-6B) includes needle hub 121, optionally comprising a female Luer connection member as shown, a needle shaft 122, and an external stopper 123. A needle lumen 124 extends between a needle proximal end 125 and a needle distal end 126; needle distal end 126 includes a size transitional portion 127 ending with a sharp needle distal tip 128. Size transitional portion 127 refers to the distal end portion of needle 105 along which there is a change, sudden or gradual, in dimensions relative to general shaft 122 dimensions, such as change in diameter or change in circumference length, for example a bevel or a chamfer. Size transitional portion is at least 1 mm in length, optionally about 3 mm. External stopper 123 is configured to physically suppress or block penetration of needle distal tip 128 in a penetrated organ beyond a predetermined length. External stopper 123 is in a form of a tube extending externally along at least part of needle shaft 122, with a stopper distal end 129 thereof located proximally to needle distal tip 128. Stopper distal end 129 is optionally fixedly positioned, although it may be selectively shiftable along length of needle shaft 122 proximally to size transitional portion 127.

Figure 8A:
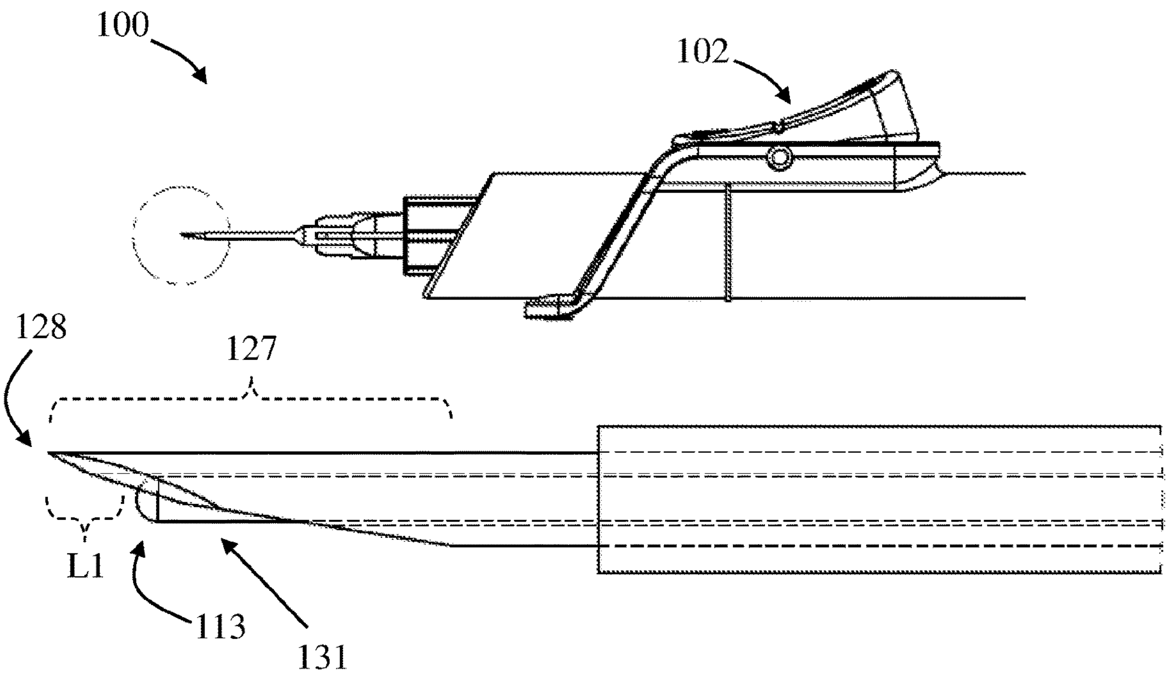
FIGS. 8A-8C illustrate side views of a distal portion of the exemplary device shown in FIG. 1C, showing different preset positions of separator distal tip relative to needle distal end, according to some embodiments of the invention.
Figure 8B:
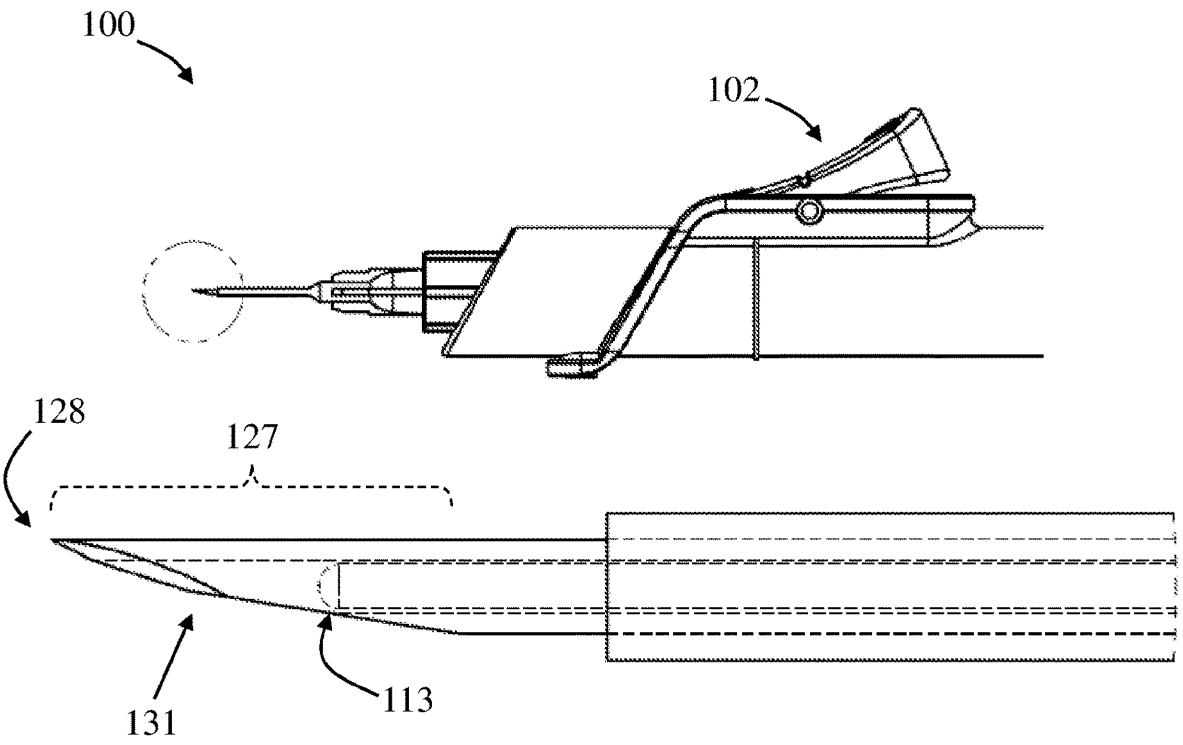
Figure 8C:
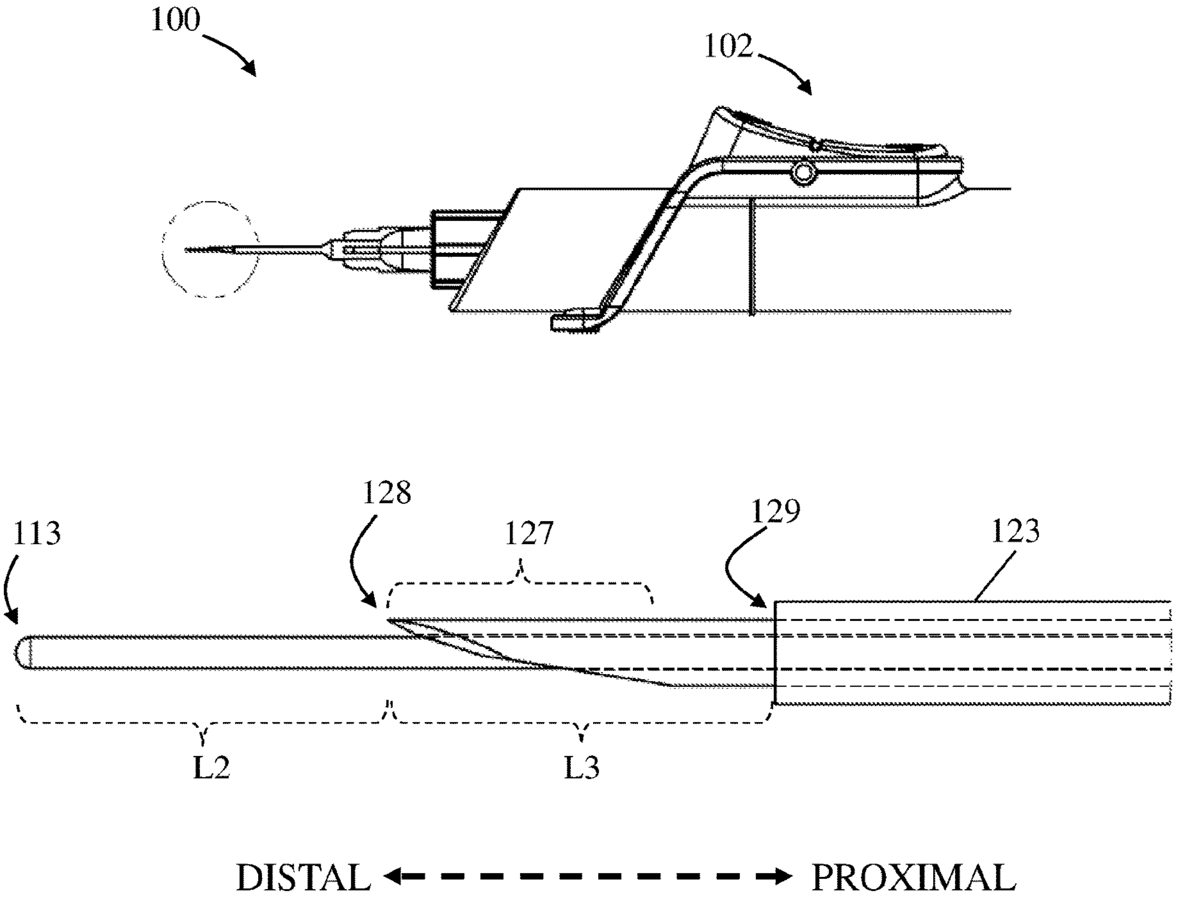

Reference is now made to FIGS. 8A-8C which illustrate side views of a distal portion of device 100, showing different preset positions of separator distal tip 128 relative to needle distal end 126. The elongated tissue separator 103 is sized and configured to extend in and throughout needle lumen 124 such that separator distal tip 113 is in juxtaposition with needle distal end 126. Actuator 101 is configured to facilitate selective shifting of tissue separator 103 in needle lumen 124 such that separator distal tip 113 is movable between several preset fixed positions relative to needle distal tip 128. Device 100 is configured such that cannula distal end 112 is positioned within, or distally to, seal 120 in each of the preset fixed positions in order to prevent leakage during the entire use of the device.

One of the preset fixed positions is an intermediate position (shown in FIG. 8A, for example), wherein switch 102 is provided in a nominal position and separator distal tip 113 is fixedly positioned and located a 'first' predetermined length L1 proximally to needle distal tip 128, optionally within a range of about 0.2 mm to about 1.5 mm, optionally about 0.5 mm. In the intermediate position, separator distal tip 113 protrudes from a laterally uncovered section 131 of transitional portion 127. Separator distal tip 113 is blunt, optionally rounded shaped, and configured to physically suppress or block penetration of size transitional portion 127 in the penetrated organ being greater than the first predetermined length, when it is fixed in the intermediate position.

Another preset fixed position is a distal-most position (shown in FIG. 8C, for example), wherein switch 102 is provided in a 'first' pressed position and separator distal tip 113 is fixedly positioned distally to needle distal tip 128. When in the distal-most position, separator distal tip 113 is located a 'second' predetermined length L2 distally to needle distal tip 128, optionally about 1 mm or more, optionally about 2 mm.

A third optional preset fixed position is a proximal-most position (shown in FIG. 8B, for example), wherein switch 102 is provided in a 'second' pressed position and separator distal tip 113 is entirely concealed in needle lumen 124 proximally to laterally uncovered section 131 of size transitional portion 127.

External stopper 123 is configured to physically suppress or block penetration of the needle distal tip in the organ over a 'third' predetermined length L3 (shown in FIG. 8C), which equals the longitudinal distance between needle distal tip 128 and stopper distal end 129, and is optionally at least 1 mm, optionally about 3 mm in length.

Figure 8D:
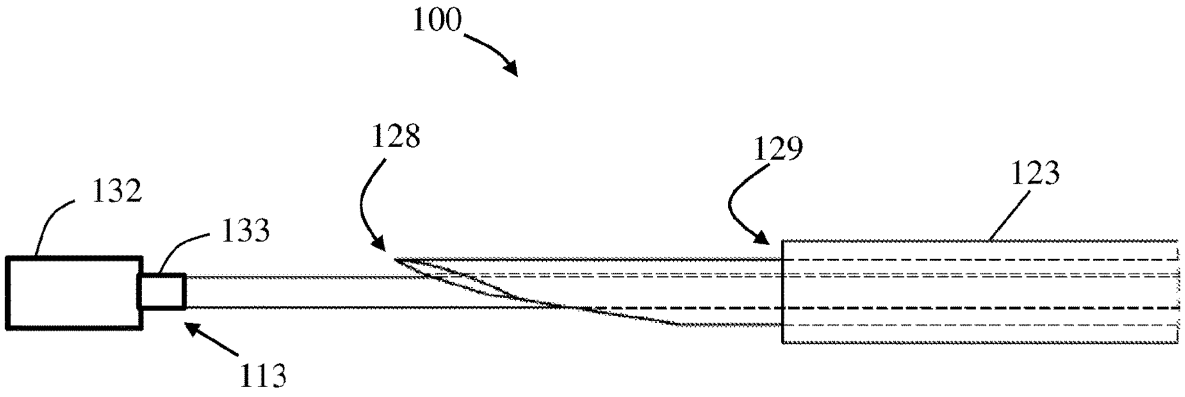
FIG. 8D illustrates a side view of a variation of the exemplary device shown in FIG. 1C configured for carrying and deploying an implant, according to some embodiments of the invention.

FIG. 8D illustrates a side view of a variation of device 100 that is configured for carrying and deploying an implant 132. In some embodiments, separator distal tip 113 includes an implant connector 133 configured for selectively hold or release implant 132, such as according to user selection. Implant connector 133 may include a threaded portion for threading to implant 132, a hook mechanism for anchoring to implant 132, or any other connection means or mechanism known in the relevant art. Implant 132 may be intended, for example, for improving or replacing a natural part or portion of an eye (e.g. an artificial retina), or it may be configured for containing medication and, for example, facilitating slow or/and controlled release of medication therefrom in/around the implantation site. Implant 132 delivery may be accomplished by first creating a passage (such as passage PSG shown in FIG. 12N, for example) formed by needle 105 or/and tissue separator 103, and then carrying and deploying implant 132 in the passage using tissue separator 103 with implant connector 133, or using other means. Optionally and alternatively, the passage is formed by pushing implant 132 therein, in such alternative the implant 132 is shaped with a blunt distal end or sharp distal end or equipped with tissue cutting element(s), and is disconnected from device 100 after forming the passage. Implant 132 may be removed from the body (eye) after required function or end result is met, or it can be left permanently in the body (eye), optionally biodegrading in the body after a period of time.

Figure 9A:
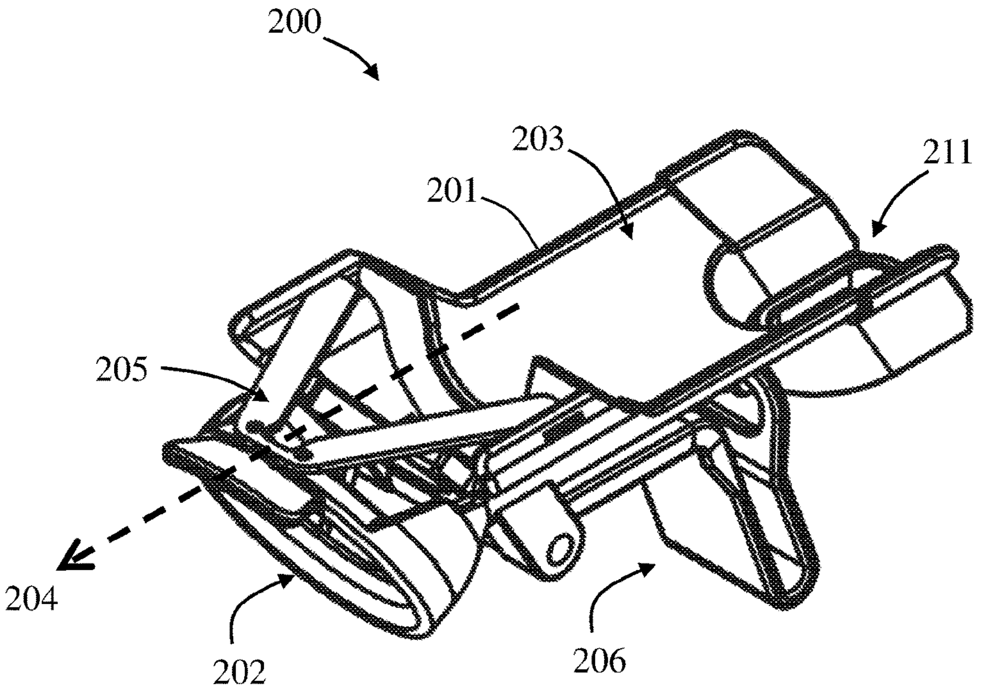
FIGS. 9A-9B respectively illustrate an isometric view and a side cut view of an exemplary organ docking device, according to some embodiments of the invention.
Figure 9B:
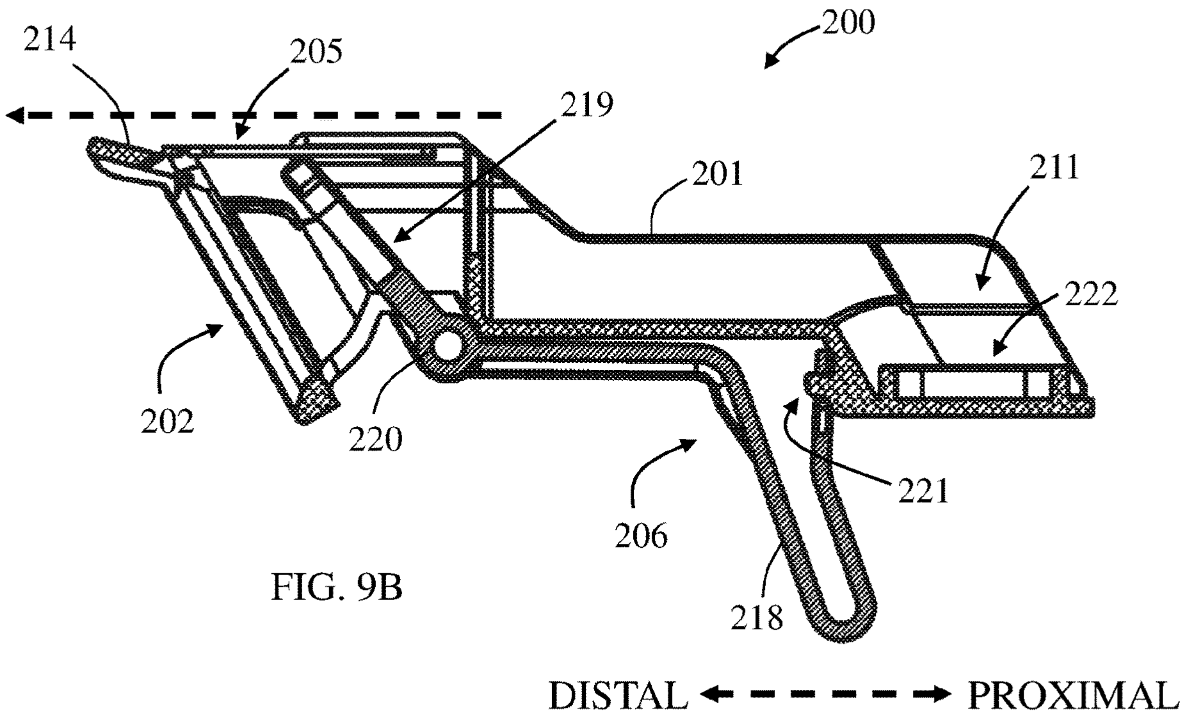

Reference is now made to FIGS. 9A-9B, which respectively illustrate an isometric view and a side cut view of organ docking device 200. Organ docking device 200 includes an organ docking device body 201 which comprises an organ contact surface 202, shaped in accordance with curvature topography of a target tissue portion, in this example in a form of a ring having a cross section curved to fit over an eyeball.

Organ docking device body 201 also includes a needle directing surface 203 configured to mark or confine a predetermined needle penetration path 204 across organ contact surface 202 for passing organ affecting device 100 therealong. In the current exemplary embodiments, needle directing surface 203 is fixedly angled to organ contact surface 202, although in other embodiments it can be selectively tiltable relative thereto. Needle directing surface 203 is shaped to fit a section of actuator 101 of organ affecting device 100, thereby confining sliding thereon to predetermined needle penetration path 204.

In this exemplary embodiment, needle directing surface 203 is formed as an elongated concave surface fixedly inclined to said organ contact surface, for facilitating tangential orientation thereof relative to an eyeball that is in contact with an anterior portion thereof with organ contact surface 202.

An elongated recess 211 is provided at proximal portion of organ docking device body 201, configured in shape and dimensions to facilitate snug fitting therein of aligning element 130 of actuator 101, thereby fastening thereto and affect alignment to the predetermined needle penetration path 204. Elongated recess 211 also serves as a penetration restricting element configured to prevent distal advancement of organ affecting device 100 along needle directing surface 203 beyond a predetermined maximal travel length. Organ docking device body 201 may also include a magnet 222 or other means configured for forcing snug fitting between needle directing surface 203 and actuator 101.

Figure 10A:
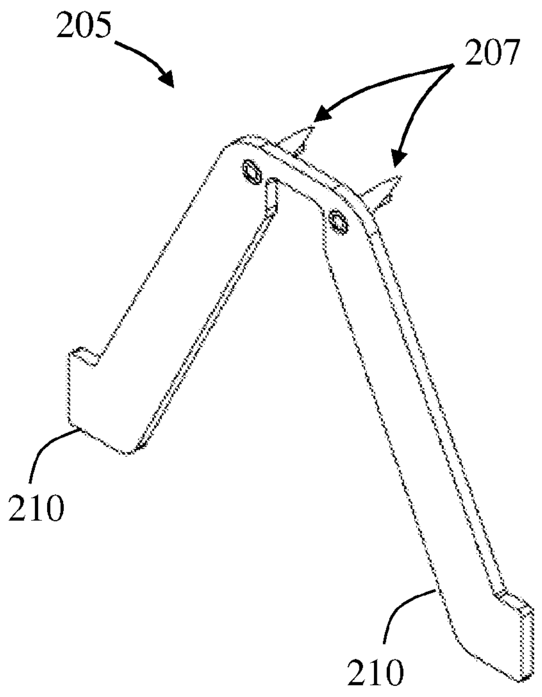
FIGS. 10A-10B respectively illustrate an isometric view and a side view of an exemplary anchoring member, according to some embodiments of the invention.
Figure 10B:
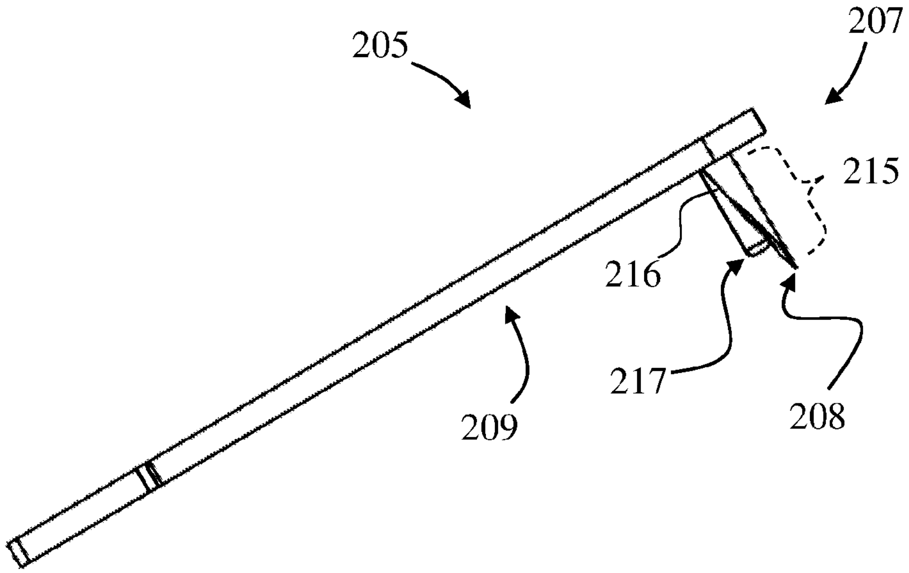

Organ docking device 200 further includes an anchoring member 205 (shown separately in FIGS. 10A-10B) and an anchoring actuator 206. Anchoring member 205 is configured to anchor to the target tissue portion (e.g., a target sclera portion), when organ contact surface 202 is in proper contact with the target tissue portion. Anchoring member 205 comprises two anchors 207 provided peripherally spaced and symmetrically opposing each other, optionally peripherally spaced with each other within a range of 0.5 mm and 3 mm.

Figure 11A:
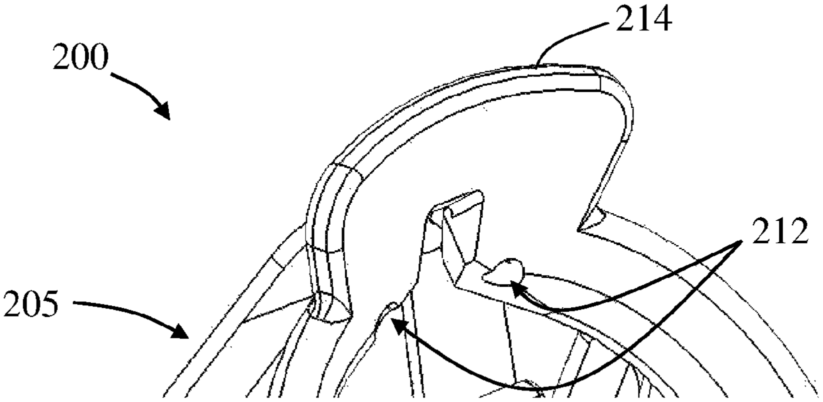
FIGS. 11A-11B illustrate frontal isometric views of the exemplary organ docking device shown in FIG. 9A, showing anchors in a withdrawn position (FIG. 11A) and in an anchoring position (FIG. 11B), according to some embodiments of the invention.
Figure 11B:
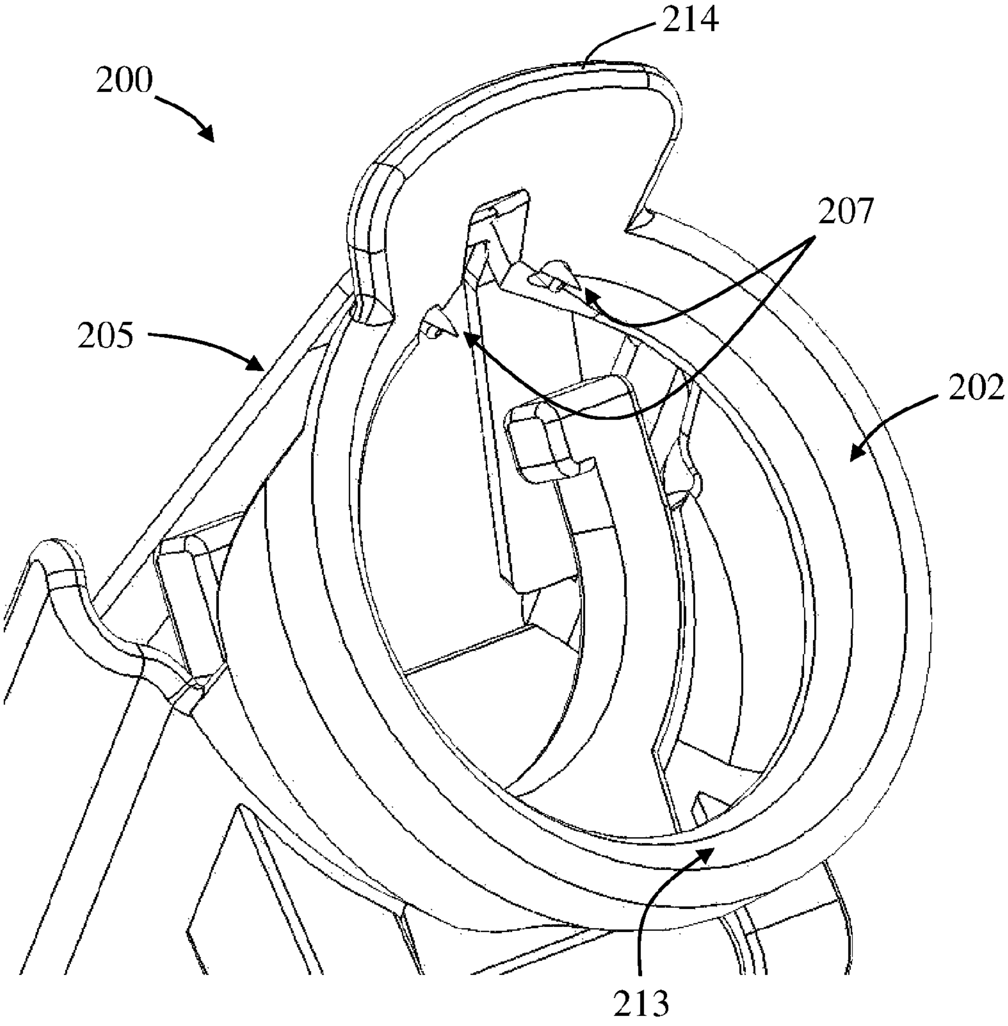

Each anchor 207 comprises a sharp anchor tip 208 configured for penetrating into the target tissue portion. Anchors 207 are projected perpendicularly from a base surface 209 formed by two anchoring members legs 210, which are spaced with each other and symmetrically arranged so as to accommodate portion of tissue affecting device 100 positioning therebetween, and for providing orientation marking of predetermined needle penetration path 204. Anchoring member 205, with anchors 207 fixated thereto, is rotationally connected to organ docking device body 201 thereby facilitating anchors motion between a withdrawn position (shown in FIG. 11A) and an anchoring position (shown in FIG. 11B).

Anchoring actuator 206 is configured to facilitate selective shifting of anchoring member 205 between the withdrawn position, in which anchoring member 205 is prevented from physically interacting with the target tissue portion, and the anchoring position, in which anchoring member 205 is anchored to the tissue target portion. Anchoring actuator 206 includes a manually operable anchoring trigger 218 configured to drive anchors 207 to shift between the withdrawn position and the anchoring position. Trigger 218, in this exemplary embodiment, is made of an elastic material and configured for manual pressing in forward direction (proximal to distal) from a nominal position, in which trigger 218 is less elastically stressed and anchoring member 205 is in the withdrawn position, to a forward position, in which trigger 218 is more elastically stressed and anchoring member 205 is in the anchoring position, such that trigger 218 can bounce back from forward to nominal position upon release. Trigger 218 is connected to anchoring member 205 via a trigger arm 219 about a trigger pivot connection 220, such that pressing forward trigger 218 results in forward (proximal to distal) shift of anchoring member 205, and protrusion of anchors 207. A trigger lock 221 interacts with anchoring trigger 218 by way of slot-lock configuration, for example, such that anchoring trigger 218 is fixedly locked in-place by trigger lock 221 when shifted to at least one of nominal position, withdrawn position and forward position, until trigger lock 221 is selectively unlocked by the user.

When anchored to the organ, organ docking device 200 facilitates generation of counteracting forces to the anchored organ during penetration into the target tissue portion with needle 105, when it is pushed along predetermined needle penetration path 204. Each anchor tip 208 is positioned proximally to organ contact surface 202 when in the withdrawn position, and distally to organ contact surface 202 when in the anchoring position for anchoring to the target tissue portion.

In a current exemplary embodiment, anchors 207 are passable through dedicated openings 212 (FIG. 11A) located at an upper peripheral portion of organ contact surface 202. When in the anchoring position, each anchor 207 protrudes via its respective opening 212 and directed generally towards an opposing peripheral point 213 of contact organ surface202 and pointed with anchor tip 208 distally in an angle to predetermined needle penetration path 204, optionally within a range of 45° to 135°, optionally approximately 90°.

Organ docking device 200 includes a tissue pressing member 214 configured for pressing against the target tissue portion, optionally particularly at a peripheral region thereof, when it is in contact with organ contact surface 202. When used for treating an eye, tissue pressing member 214 is configured for pressing more deeply against periphery of the target sclera portion for fastening or tightening the conjunctiva adjacent to the target sclera portion, thereby reducing resistive or recoil forces applied to needle distal tip 128 when piercing the target sclera portion.

Organ docking device 200 and organ affecting device 100 are configured such that when actuator 101 and needle 105 follow predetermined needle penetration path 204 along needle directing surface 203, needle distal tip 128 is confined to passing between the two anchors 207 in proximity to anchor distal tip 208 of each. Each anchor 207 has an anchor size transitional portion 215 (e.g., in a beveled portion) ending with anchor distal tip 208. For restricting a maximal penetration depth, each anchor 207 is provided with a slender restrictor 216 with a blunt restrictor tip 217 thereof fixedly positioned between ends of anchor size transitional portion 215 and is protruding from a laterally uncovered section of size transitional portion 215.

Figure 12A:
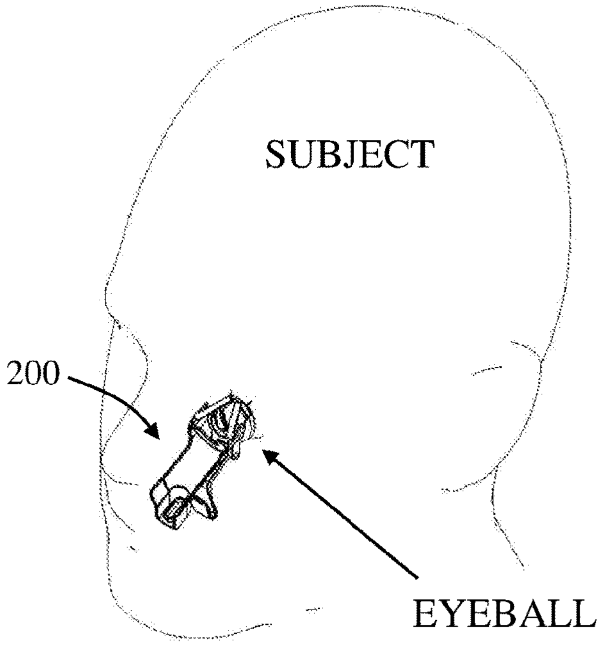
Figure 12B:
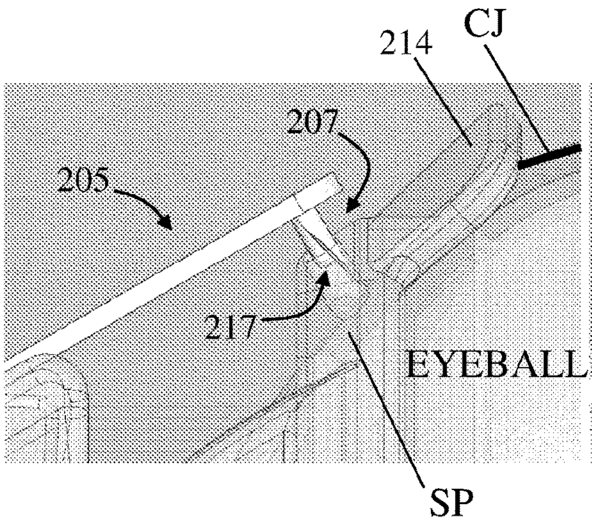
Figure 12C:
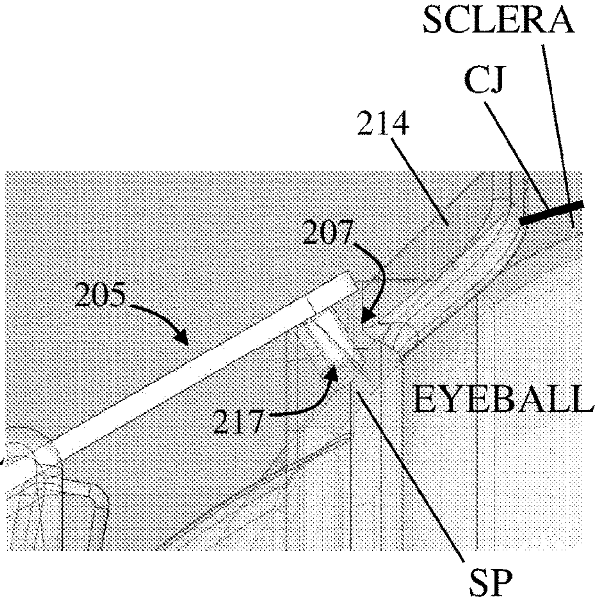
Figure 12D:
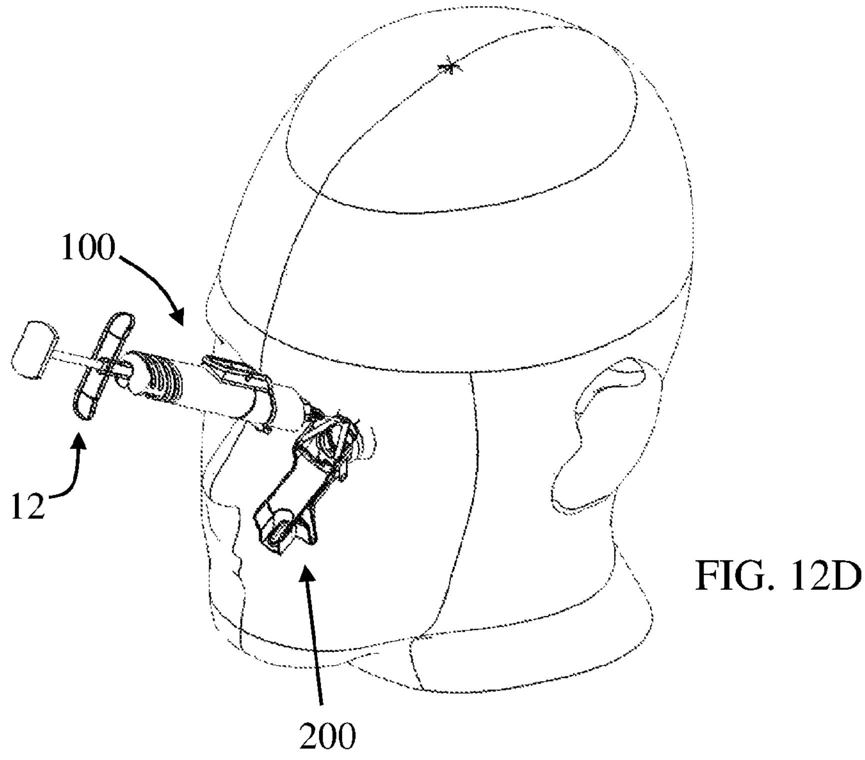
Figure 12E:
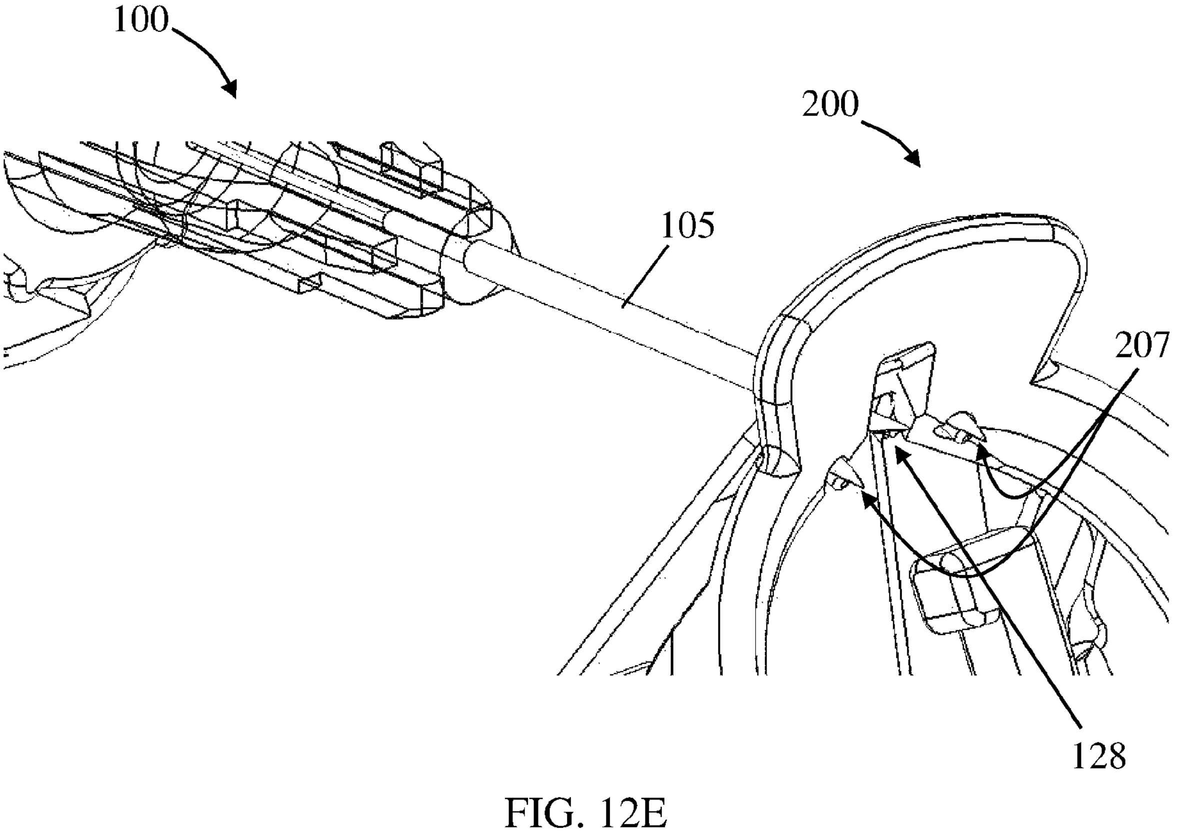
Figure 12F:
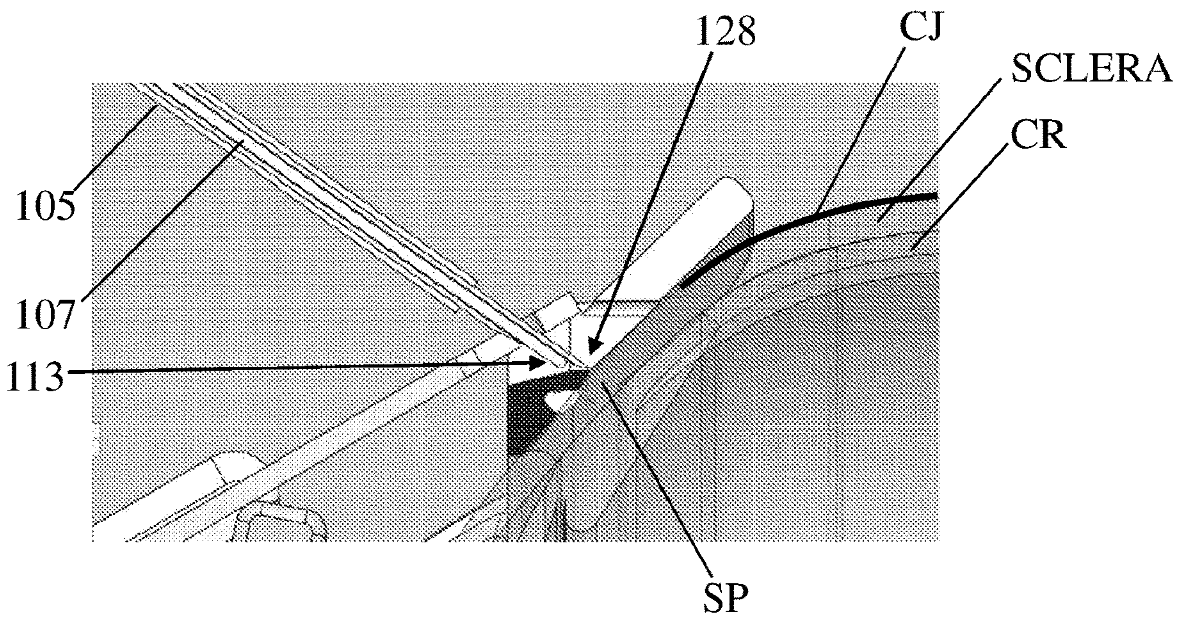
Figure 12G:
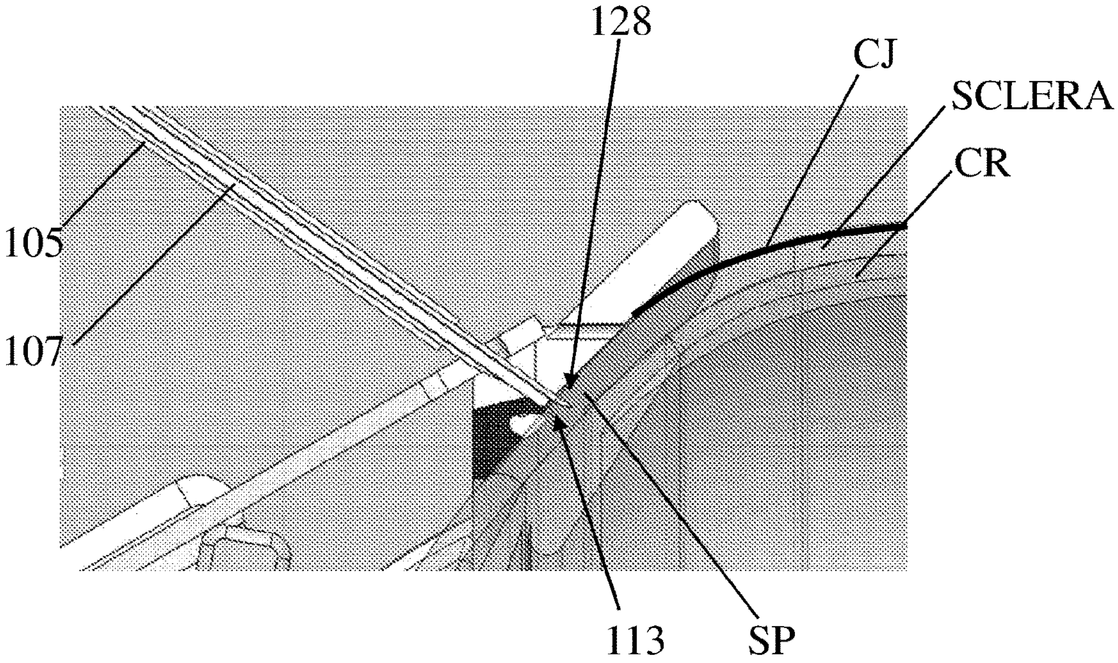
Figure 12H:
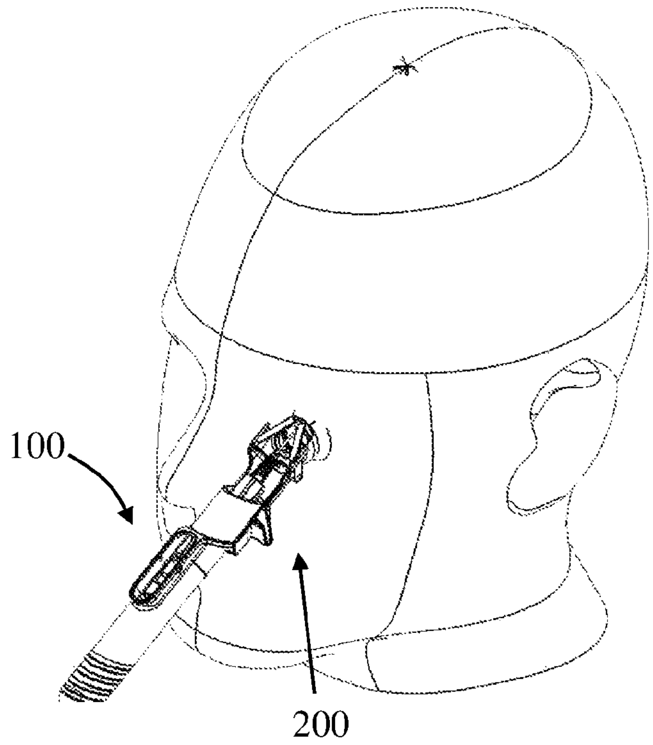
Figure 12I:
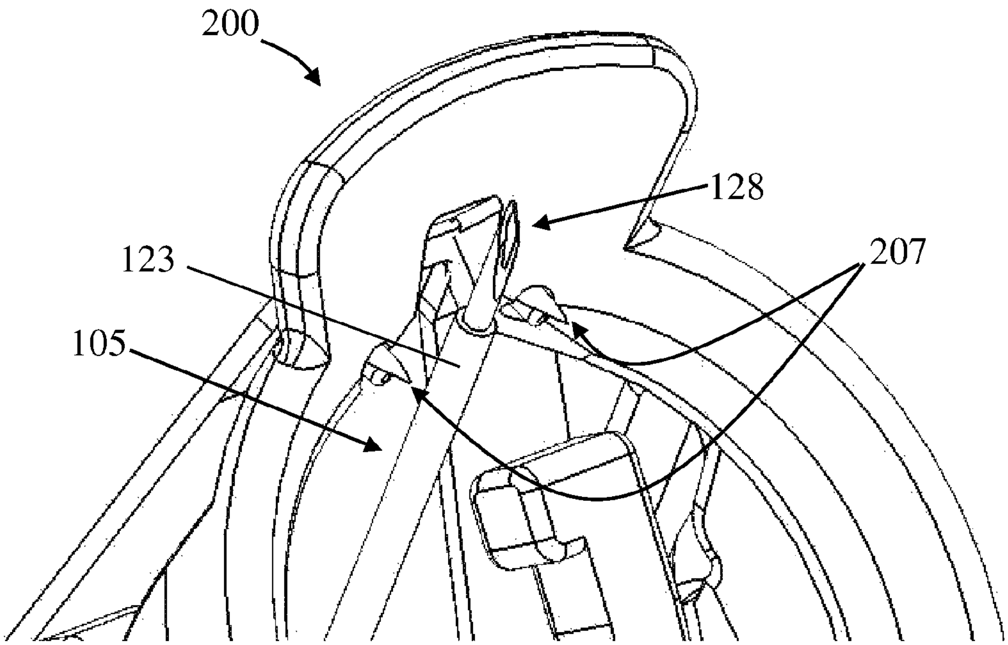
Figure 12J:
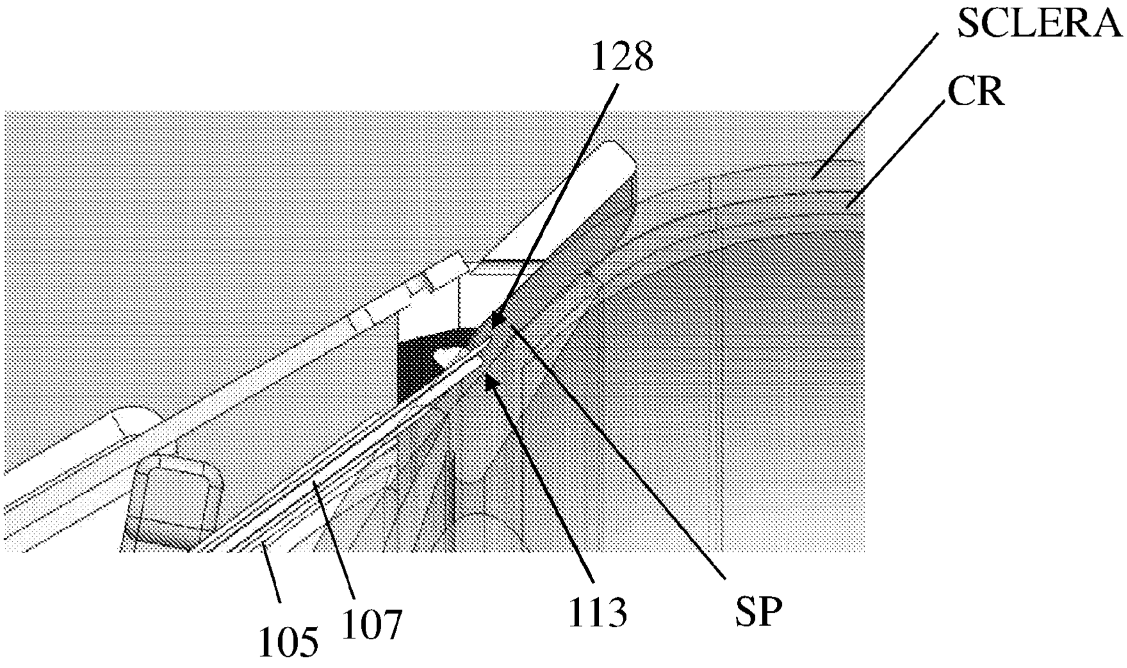
Figure 12K:
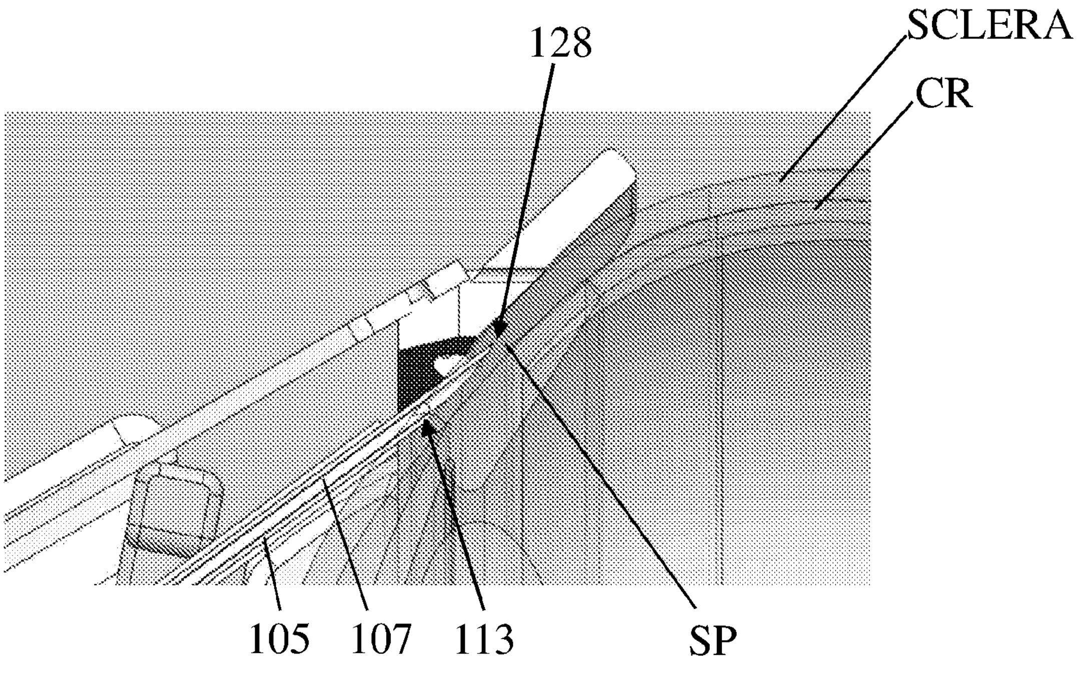

FIGS. 12A-120 illustrate views of kit 10, system 11 organ affecting device 100 or/and organ docking device 200 in different configurations representing exemplary steps in a method for fixating a sclera portion, directing needle penetration into the sclera portion, and facilitating fluid injection to an interlayer region in an eye of a subject. The first group of steps is intended for fixating a target tissue portion (in this example a sclera portion SP) of an organ (eyeball) and directing needle penetration into the target tissue portion, using organ docking device 200.

As illustrated in FIG. 12A, organ docking device is positioned in a location chosen by the user (an ophthalmologist, for example) and organ contact surface 202 is positioned against and in contact with target sclera portion SP. Placing of organ docking device 200 is performed symmetrically around the limbus (which is the area of transition from clear cornea to opaque sclera) in a chosen eye quadrant. Since the sclera is considered structurally anisotropic, although tangential penetration of the needle 105 is desired for facilitating the requested injection direction, an initial perpendicular penetration is preferred in order to minimize forces resistive to needle puncture and travel in the sclera. After initial perpendicular penetration, the needle is shifted and advanced in the sclera in a path tangential (or close to tangential) to the choroid until reaching the target injection site in the interlayer region within the choroid layers. Penetration to the sclera is done using the needle tip, while penetration into the choroid is done using the blunt tissue separator, for avoiding or minimizing potential (unintentional) damage to blood vessels located within the choroid.

Figure 12L:
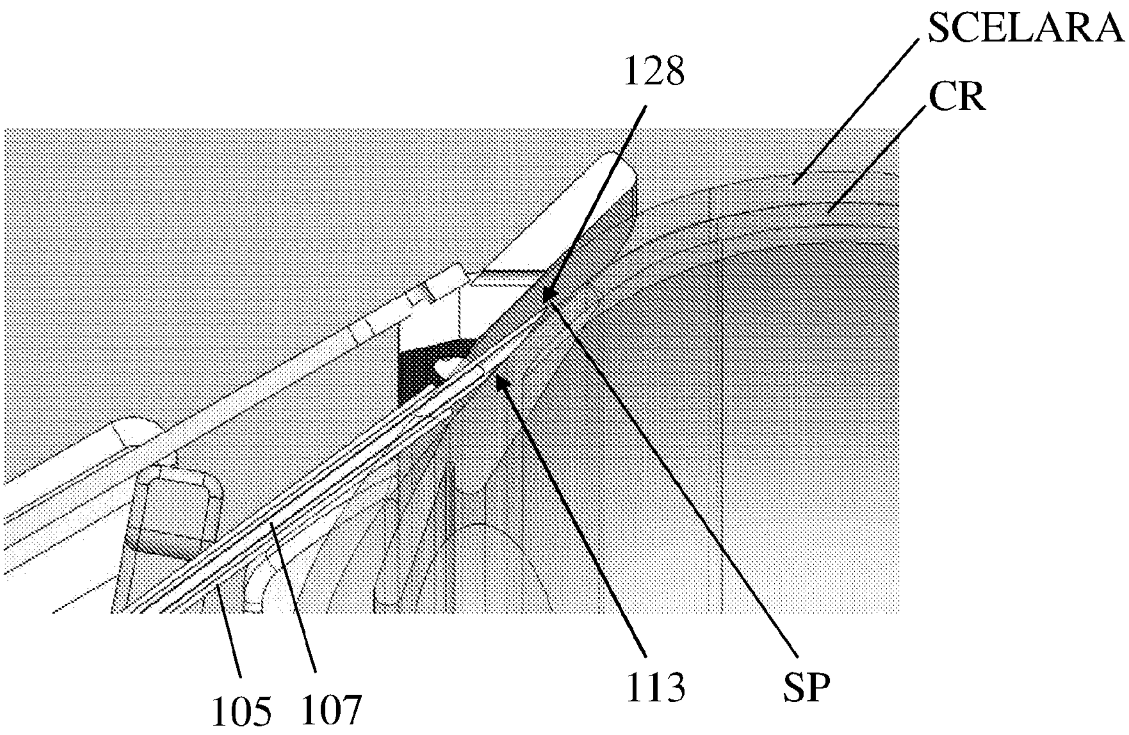

The point of penetration from the sclera to the choroid is distanced from the point of penetration into the sclera relative to organ contact surface202 (see FIG. 12L, and FIG. 9A-more distal along path 204). Such a distance is important to the sealing effect created by injecting medication through a passage PSG in choroid CR: After injection, hydrostatic pressure in the eye would tend to force the injected medication to flow back, however, the sclera portion proximal (relative to eye globe) to the penetration to the choroid is intact, so that back flow is prevented, and the entire passage PSG thus acts a one-way valve preventing the medication to reflux from the perpendicular penetration to the sclera portion.

When the organ docking device 200 is positioned symmetrically around the limbus, the user is indicated by the organ docking device to perpendicularly penetrate the needle 105 into the sclera portion 2 mm to 4 mm posterior to limbus (See FIG. 12E, needle tip 128 should be inserted in the opening between anchors 207). Distances from the limbus are: pars plicata 1-2 mm, pars plana about 4 mm anterior-posteriorly. This ensures that the perpendicular penetration to the sclera portion will be given proximally (relative to eye globe) to the pars plana, and that the tangential penetration will result in penetration of the separator into the choroid.

Although perpendicular penetration into the sclera portion is partial (not all the way through the sclera), perpendicular penetration proximally into the pars plana relative to the eye globe is a safety measure. Perpendicular penetration into the sclera portion more anteriorly may result in hemorrhage due to trauma to the highly vascularized pars *plicata*. A perpendicular penetration to the sclera portion more posteriorly may result in retinal detachment.

Anchoring member 205 is provided in a withdrawn position (FIG. 12B) so, after positioning, anchoring actuator 206 is then applied to shift anchoring member 205 to anchoring position (FIG. 12C) for anchoring to the target sclera portion. As shown, anchors 207 penetrate approximately perpendicularly into the sclera layer, at the chosen target portion thereof, about 0.5 mm deep, until the blunt restrictor tips 217 contact the outer surface of the sclera and suppresses further advance (at least in a magnitude noticeable by the user, as a sign for him to stop advancing forward). While organ contact surface 202 is in contact with sclera portion SP, tissue pressing member 214 presses against an upper periphery of the target sclera portion and tightens the conjunctiva CJ adjacent to target sclera portion SP.

Once deployed in a chosen position against target sclera portion SP, organ docking device 200 can serve for directing organ affecting device 100 with needle 105 for penetrating (piercing) with needle distal tip 128 into sclera portion SP along predetermined needle penetration path 204, while countering forces generated between organ docking device body 201 and the eyeball (for preventing revolving of the eyeball) during sclera penetration.

The next group of steps is intended for facilitating fluid injection to an interlayer region in an eye of a subject. The requested result, as previously described, is an artificially formed passage or channel, oriented at a shallow angle, approximately tangentially to the target sclera portion SP adjacent to needle entry point, and extends about 2 mm to 4 mm in length from within sclera layer into the choroid. The passage, once cleared from objects, creates a directional space in the interlayer region of the choroid and adjacent layers, which can then be filled with fluid (medication) which then disperses throughout the interlayer region space including posterior portions remote from the formed passage.

Before applying organ affecting device 100, the user has to verify that switch 102 is in its nominal position so that separator distal tip 113 is fixedly positioned at the intermediate position, with first predetermined length L1 proximally to needle distal tip 128, and protrudes from a laterally uncovered section 131 of size transitional portion 127 (as shown in FIG. 8A). First predetermined length L1 is shorter than a thickness of said sclera, optionally within a range of 0.2 mm to 1.5 mm, optionally about 0.5 mm in length. With separator distal tip 113 at the intermediate position, organ affecting device 100 is applied (FIG. 12D) in order to penetrate into (but not throughout) the sclera portion SP using needle distal tip 128 until contacting the eye outer surface with separator distal tip 113 (FIGS. 12E-12G). As shown, sclera penetration is performed at a penetration angle within a range of 30° to 120°, optionally perpendicularly, relative to eye outer surface adjacent to needle penetration point, between the two anchors 207.

Once needle distal tip 128 is at a depth equal to the first predetermined length L1 in sclera portion SP, it is then maneuvered from the steep penetration angle to a shallow injection angle, within a range of 0° to 30° s, optionally tangentially, to the eye outer surface adjacent to the penetration point (as shown in FIGS. 12H-12J). Organ docking device 200 is configured with needle directing surface 203 angled to organ contacting surface 202, such that needle distal tip 128 maneuvering is accomplished by positioning actuator 101 on top of and along needle directing surface, with the needle distal tip 128 pointing towards the sclera portion SP in the direction of predetermined needle penetration path 204 (with the beveled portion of needle 105 positioned towards the eye). To secure orientation of needle 105 along predetermined needle penetration path 204, aligning element 130 of actuator 101 is fitted in elongated recess 211 of organ docking device body 201.

Following needle distal tip 128 maneuvering to the injection angle, separator distal tip 113 is withdrawn to proximal-most position (FIG. 12K), so that it is entirely concealed in needle lumen 124 proximally to laterally uncovered section of size transitional portion 127. Needle distal tip 128 can then be pushed forward in sclera (FIG. 12L) without being restricted to maximal travel length of first predetermined length L1. Since the injection angle is shallow, optionally approximately tangential to the sclera layer, the needle can advance a few millimeters deep in the sclera without penetrating through into the choroid, for example along a length within a range of 1 mm to 5 mm, optionally of about 3 mm. Passing an allowed penetration length is suppressed or blocked with external stopper 123.

Figure 12M:
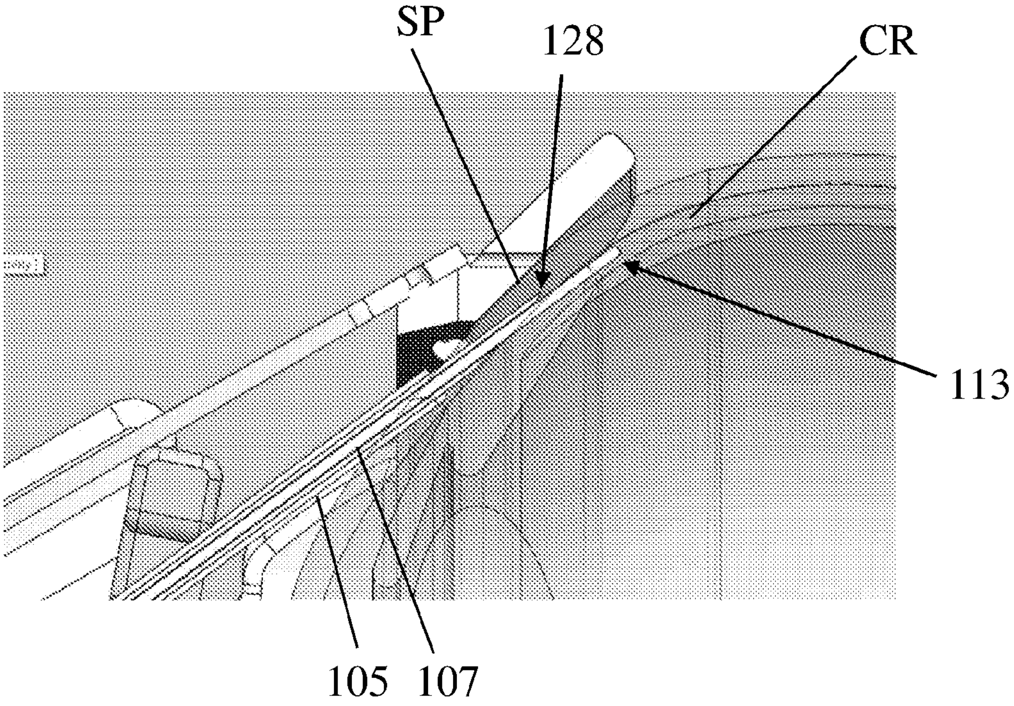
Figure 12N:
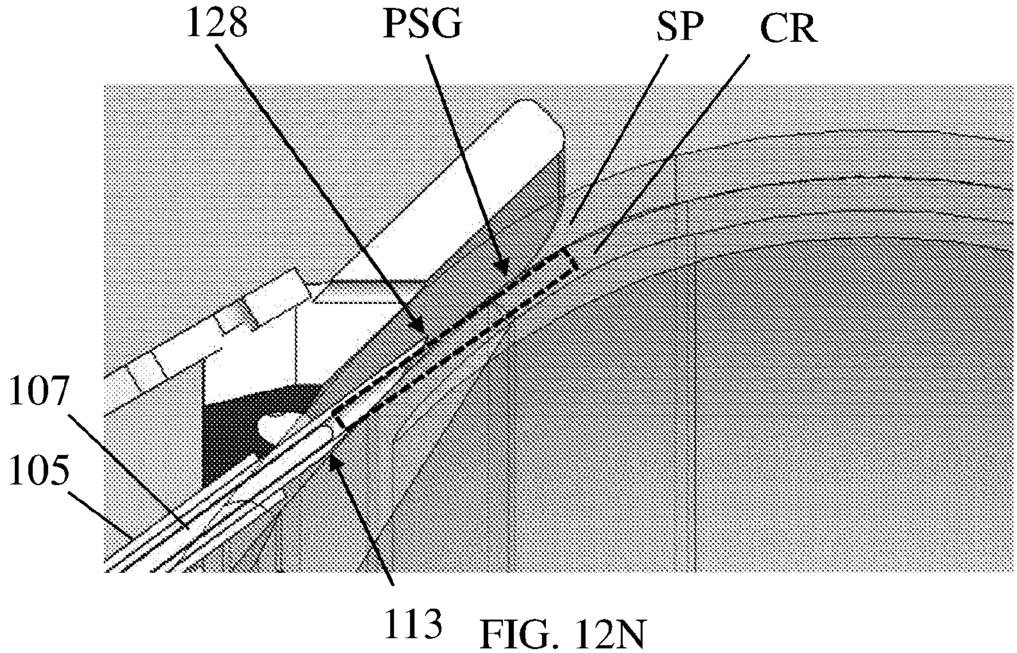
Figure 12O:
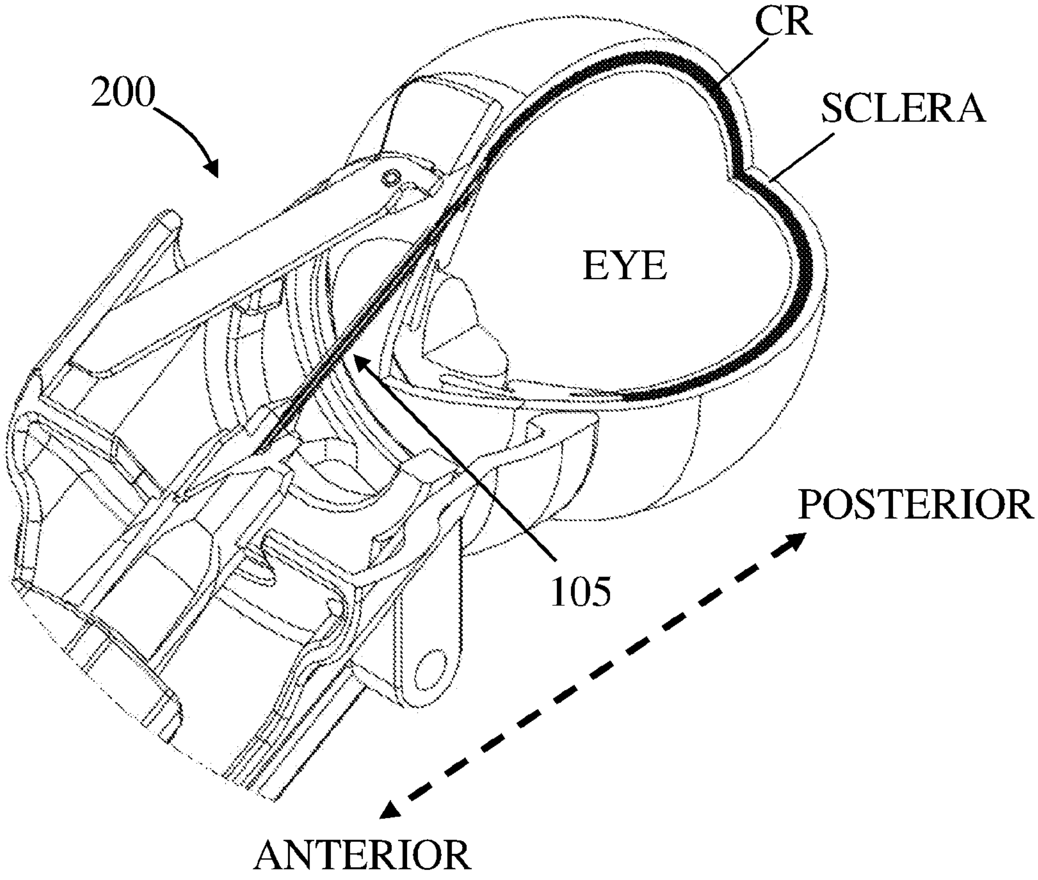

In order to create the directional passage into the choroid, use of a sharp needle is avoided in order to prevent damage to blood vessels in the choroid, so the passage is created instead with the blunt separator distal tip 113. Therefore, tissue separator 107 is shifted distally within the needle lumen 124 such that separator distal tip 113 repositions to the distal-most position (FIG. 12M), along second predetermined length L2 of at least 1 mm, optionally about 2 mm, distally to needle distal tip 128, thereby advancing in sclera portion SP, penetrating through into choroid CR and forming a passage PSG in choroid CR (shown in FIG. 12N).

Passage PSG may have a length and orientation in the eye, so as to pass in the extra-vascular choroid layer of choroid CR. Optionally, additionally or alternatively, passage PSG may have a length and orientation in the eye, so as to enlarge a suprachoroidal space distally to sclera portion SP. Optionally, additionally or alternatively, passage PSG may have a length and orientation in the eye, so as to extend between choroid CR and a retinal pigment epithelium layer adjacent thereto.

After forming passage PSG, separator distal tip 113 is withdrawn again, optionally to the proximal-most position so it is entirely concealed in needle lumen 124 (FIG. 12N), and medication can then be injected into passage PSG using syringe 12. The methods and devices described herein may be used to deliver a therapeutic composition (especially a liquid therapeutic composition) to the subretinal space (or to the extra-vascular choroidal layer of choroid, or the suprachoroidal space or between choroid and a retinal pigment epithelium layer adjacent thereto) of an animal (especially mammalian eye) such as a composition including a pharmaceutically effective amount of an active ingredient (e.g., an active pharmaceutical ingredient and/or a cell and/or a gene) in a suitable carrier.

The amount of therapeutic composition administered is any suitable amount and depends on factors such as the nature of the active ingredient, the concentration of the active ingredient, the treatment circumstances and the professional judgment of a treating physician and is readily calculable or determined by a person having ordinary skill in the art without undue experimentation. That said, typically the amount of composition administered to a human eye using the methods and devices described herein is up to about 500 microliters, up to about 300 microliters, more typically up to about 150 microliters. Typically, an amount of composition administered is between about 10 microliters and about 150 microliters. As used herein a "therapeutic composition" refers to a preparation of one or more of the active ingredients with other components such as pharmaceutically-acceptable carriers and excipients. The purpose of a therapeutic composition is to facilitate administration of an active ingredient to a subject.

The term "pharmaceutically acceptable carrier" refers to a carrier or a diluent that does not cause significant irritation to a subject and does not substantially abrogate the activity and properties of the administered active ingredients. An adjuvant is included under these phrases. The term "excipient" refers to an inert substance added to a therapeutic composition to further facilitate administration of an active ingredient.

Therapeutic compositions used in implementing the teachings herein may be formulated using techniques with which one of average skill in the art is familiar in a conventional manner using one or more pharmaceutically-acceptable carriers comprising excipients and adjuvants, which facilitate processing of the active ingredients into a pharmaceutical composition and generally includes mixing an amount of the active ingredients with the other components. Suitable techniques are described in "Remington's Pharmaceutical Sciences," Mack Publishing Co., Easton, PA, latest edition, which is incorporated herein by reference. For example, pharmaceutical compositions useful in implementing the teachings herein may be manufactured by one or more processes that are well known in the art, e.g., mixing, blending, homogenizing, dissolving, granulating, emulsifying, encapsulating, entrapping and lyophilizing processes.

Pharmaceutical compositions suitable for implementing the teachings herein include compositions comprising active ingredients in an amount effective to achieve the intended purpose (a therapeutically effective amount). Determination of a therapeutically effective amount is well within the capability of those skilled in the art, for example, is initially estimated from animal models such as monkey or pigs.

In accordance with the above, a therapeutic composition used for implementing the teachings herein includes any suitable carrier, such as phosphate buffered saline, e.g., 140 mM NaCl, 2.8 mM KCl, 10 mM sodium phosphate dibasic, 2 mM potassium phosphate monobasic with a pH of 7.4.

A therapeutic composition used for implementing the teachings herein includes any suitable active ingredient. In some embodiments, a therapeutic composition comprises at least one active ingredient selected from the group consisting of at least one of an active pharmaceutical ingredient, a cell and a gene. Suitable active ingredients include, but are not limited to, active pharmaceutical ingredients such as any of the followings.

In some embodiments, a therapeutic composition comprises inhibitors of surface glycoprotein receptors.

In some embodiments, a therapeutic composition comprises antimitotics; microtubule inhibitors; anti-secretory agents; active inhibitors; remodeling inhibitors; antisense nucleotides; anti-metabolites.

In some embodiments, a therapeutic composition comprises an anticancer chemotherapeutic agent; antiproliferatives (including antiangiogenesis agents).

In some embodiments, a therapeutic composition comprises an anti-inflammatories (such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone, triamcinolone, triamcinolone acetonide loteprednol, difluprednate, fluorometholone, or rimexolone); non-steroidal anti-inflammatoirech as salicylate, indomethacin, ibuprofen, diclofenac, flurbiprofen, piroxicam bromfenac, ketorolac tromethamine or nepafenac); antiallergenics (such as sodium chromoglycate, antazoline, methapyriline, chlorpheniramine, cetrizine, pyrilamine, prophenpyridamine); anti-proliferative agents (such as 1,3-cis retinoic acid); decongestants (such as phenylephrine, naphazoline, tetrahydrazoline); miotics and anticholinesterase (such as pilocarpine, salicylate, carbachol-9 acetylcholine chloride, physostigmine, serine, diisopropyl fluorophosphate, phospholine iodine, demecarium bromide).

In some embodiments, a therapeutic composition comprises antineoplastics (such as carmustine, cisplatin, fluorouracil); immunological drugs (such as vaccines and immune stimulants).

In some embodiments, a therapeutic composition comprises hormonal agents (such as estrogens, estradiol, progestational, progesterone, insulin, calcitonin, parathyroid hormone, peptide and vasopressin hypothalamus releasing factor); immunosuppressive agents, growth hormone antagonists.

In some embodiments, a therapeutic composition comprises growth factors and/or cytokines (such as epidermal growth factor, fibroblast growth factor, platelet derived growth factor, transforming growth factor beta, somatotropin, fibronectin, nerve growth factor, tumor necrosis factor, interleukins, ciliary neurotrophic factor).

In some embodiments, a therapeutic composition comprises inhibitors of angiogenesis (such as angiostatin, anecortave acetate, thrombospondin, inhibitors of VEGF and/or VEGF receptors, inhibitors of PDGF and/or PDGF receptors).

In some embodiments, a therapeutic composition comprises dopamine agonists.

In some embodiments, a therapeutic composition comprises radio-therapeutic agents.

In some embodiments, a therapeutic composition comprises peptides; proteins; enzymes; extracellular matrix components.

In some embodiments, a therapeutic composition comprises ACE inhibitors.

In some embodiments, a therapeutic composition comprises free radical scavengers; chelators; antioxidants.

In some embodiments, a therapeutic composition comprises anti-polymerases.

In some embodiments, a therapeutic composition comprises photodynamic therapy agents.

In some embodiments, a therapeutic composition comprises gene therapies and gene editing agents (may include but not limited to viral vectors, CRISPR/Cas9 Meganucleases, ZFNs, TALEN).

In some embodiments, a therapeutic composition comprises gene knockdown agents, such as those including RNA, which may include but not limited to SiRNA ShRNA AS-RNA such as QR110.

In some embodiments, a therapeutic composition comprises therapeutic agents such as prostaglandins, anti-prostaglandins, prostaglandin precursors, and the like.

In some embodiments, a therapeutic composition comprises an anti-angiogenic agent such as ranibizumab, bevacizumab, Aflibercept or pegaptanib, or combinations thereof.

In some embodiments, a therapeutic composition comprises an anti-vascular endothelial growth factor (anti-VEGF) agent such as Macugen, Lucentis, Avastin, Eylea, Brolucizumab, Abicipar Pegol, OPT-302 or any suitable biosimilar, bio-better or combinations thereof.

In some embodiments, a therapeutic composition comprises cross-linking agents.

In some embodiments, a therapeutic composition comprises viscous agents for short and long term buckling effect.

In some embodiments, a therapeutic composition comprises an anti-TNF alpha agent such as infliximab, etanercept, adalimumab, certolizumab or golimumab.

In some embodiments, a therapeutic composition comprises mTOR inhibitors such as sirolimus, Everolimus, Temsirolimus or a mTOR kinase inhibitor.

In some embodiments, a therapeutic composition comprises a neuro-protective agent such as an antioxidant, calcineu n inhibitor, NOS inhibitor, sigma-1 modulator, AMPA antagonist, calcium channel blocker or histone-deacetylases inhibitor.

In some embodiments, a therapeutic composition comprises a complement inhibitor such as Lampalizumab.

In some embodiments, a therapeutic composition comprises anti-platelet derived growth factor inhibitors (PDGF) such as anti-platelet agents, thrombin inhibitors, antithrombogenic agents; thrombolytic agents; fibrinolytic agents; Pegpleranib, Rinucumab, DE-120, Vorolanib (X-82, CM-082).

In some embodiments, a therapeutic composition comprises angiopoietin pathway inhibitors such as Nesvacumab (REGN-910-3), RG-7716, ARP-1536, AKB-9778.

In some embodiments, a therapeutic composition comprises antihypertensive agents such as vasospasm inhibitors, calcium channel blockers, vasodilators; Acetazolamide (URAMOX, DIAMOX).

In some embodiments, a therapeutic composition comprises Antimicrobial agents and antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), anti-fungals (such as amphotericin B and miconazole).

In some embodiments, a therapeutic composition comprises anti-virals such as idoxuridine trifluorothymidine, acyclovir, gancyclovir, interferon, anti AIDS CMV. In some embodiments, a therapeutic composition comprises alternative targets as ICON-1 (hI-con1)-0.3 mg intravitreal injection, Carotuximab (DE-122, TRC105).

In some embodiments, a therapeutic composition comprises TOXINS such as Botulinum toxin.

In some embodiments, a therapeutic composition comprises tissue targeting agent such as Brilliant blue, antibodies or other small molecules for tissue targeting.

In some embodiments, a therapeutic composition comprises cross linking agents.

In some embodiments, a therapeutic composition comprises controlled drug release formulations, such as, but not limited to, PEGylation, Hydrogel Depot, non-biodegradable fluorescent polystyrene particles, biodegradable formulations.

In some embodiments, a therapeutic composition comprises a cell therapy facilitator, such as but not limited to stem cells, a forebrain-derived human cortical neural progenitor cell, a retinal progenitor cell, a mature photoreceptor cell, and an RPE cell. In some embodiments, the stem cell is selected form the group consisting of hippocampal stem cells, embryonic stem cells, bone marrow stem (stromal) cells and retinal stem cells.

In some embodiments, the teachings herein are used and/or implemented for the treatment of disorders of the eye such as retinitis pigmentosa, macular degeneration (including atrophic macular degeneration), Best's disease, Stargardt's disease, Sorsby's disease, juvenile macular degeneration, central areolar choroidal dystrophy, central serous chorioretinopathy, choroidermia, choroidal melanoma, Coat's disease, cone-rod dystrophy, corneal dystrophy, Fuch's dystrophy, cystoids macular edema, diabetic retinopathy, Doyne honeycomb retinal dystrophy, hypertensive retinopathy, glaucoma, juvenile retinoschisis, lattice degeneration, Leber's miliarly aneurism, ocular histoplasmosis, ocular ischemic syndrome, papillophlebitis, polypoidal choroidal vasculopathy, toxoplasmosis, and Usher syndrome, vascular occlusions, inflammations such as uveitis, choroiditis and retinistis, and various tumors including neoplasms.

In some embodiments, the teachings herein are implemented to treat a disease of the eye. In some embodiments, the disease of the eye treated in accordance with the teachings herein is atrophic macular degeneration, and the therapeutic composition comprises stem cells as an active ingredient in a carrier such as PBS.

In some such embodiments, a concentration of between about 10,000 and about 1,000,000 cells/microliter, in some embodiments between about 200,000 and about 400,000 cells/microliter and in some embodiments between about 250,000 and about 350,000 cells/microliter.

In some such embodiments, when the subject is human, between about 1 microliter and about 500 microliters, and in some embodiments between about 100 microliter and about 300 microliters, of therapeutic composition is administered. Embodiments of the invention have been described herein primarily with reference to treatment of living human subjects. It is understood, however, that embodiments of the invention are performed for the veterinary or industrial (agriculture) treatment of a non-human mammal, such as pigs and other porcines, dogs and other canids, cats and other felines, horses and other equines, monkeys, apes and bovines.

The medication or/and agent thereof is optionally selected from a group consisting of (but not limited to): inhibitors of surface glycoprotein receptors, antimitotic agents, anticancer chemotherapeutic agents, anti-inflammatory agents, nonsteroidal anti inflammatory agents, antineoplastic agents, hormonal agents, growth factors, inhibitors of angiogenesis, dopamine agonists, radiotherapeutic agents, peptides; proteins; enzymes; extracellular matrix components, ACE inhibitors, free radical scavengers, anti-polymerases, photodynamic therapy agents, gene therapy and gene editing agents, anti-angiogenic agent, VEGF and VEGF receptor inhibitors, PDGF and PDGF receptor inhibitors, DNA, RNA, antisense RNA, viruses, exosomes, toxins, cross linking agents, tissue targeting agents, sustained release systems, antihypertensive agents, Antimicrobial agents, Antiviral, cells, antibiotics, Controlled drug release formulations, nucleic acid based therapeutic, mTOR inhibitors, an anti-TNF alpha agent, a vascular permeability inhibitor, Complement inhibitor or combinations thereof. The medication may be in the form of Low-to-high viscosity and low-to-high-volume of suspension, emulsion, solution, gels, Nano therapies, microspheres, or in the form of inserts or implants. A total volume and/or flow rate of medication injection can be set, for example a total volume greater than 10 μL. Optionally, passage PSG is flooded with a total volume of medication greater than 100 μL, optionally up to 500 μL. FIG. 120 illustrates the result of passage PSG flooding, showing that the entire interlayer region between the choroid and retina is filled with medication.

Figure 13A:
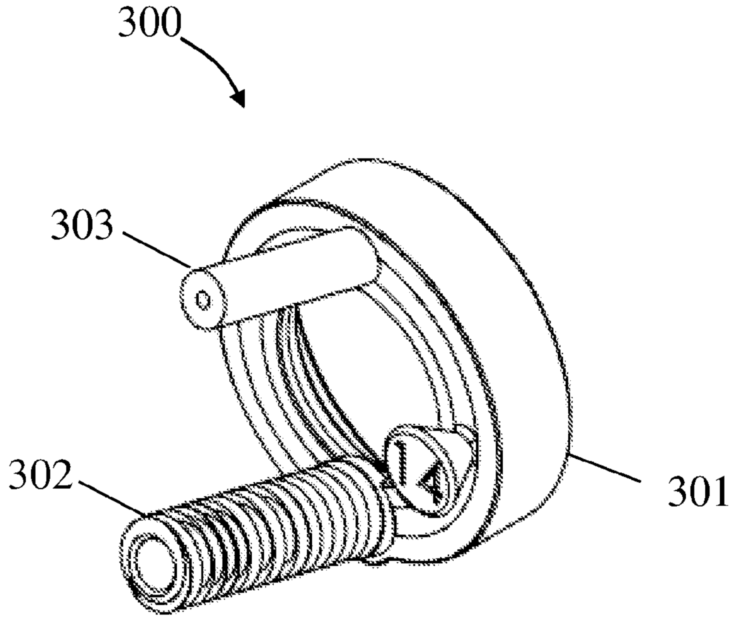
FIGS. 13A-13B respectively illustrate isometric view and side cut view of an exemplary organ docking device employing vacuum attachment means, according to some embodiments of the invention.
Figure 13B:
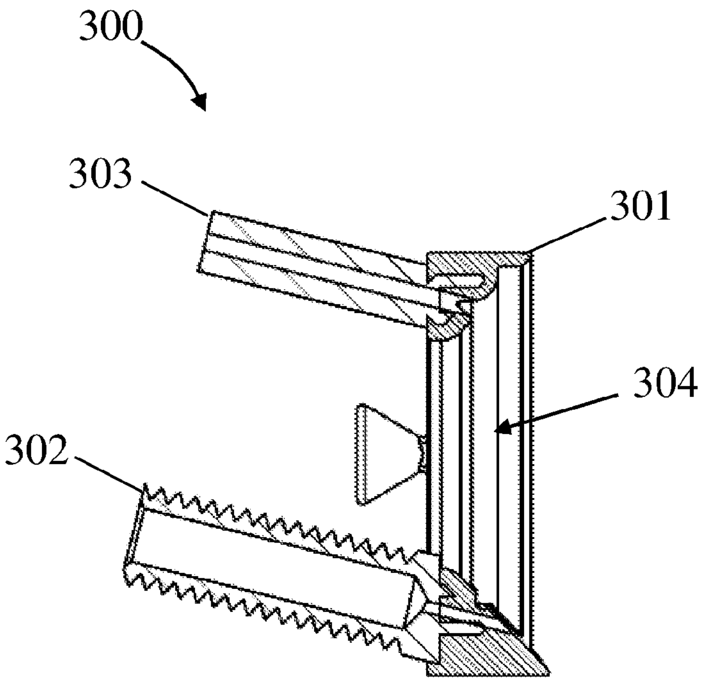

FIGS. 13A-13B respectively illustrate an isometric view and side cut view of an exemplary organ docking device 300 which is optionally an exemplary variation of organ docking device 200. Organ docking device 300 includes an eye docking element301, a first port 302 configured for accommodating and connecting to a distal portion of an organ affecting device (such as organ affecting device 100, for example) and a second port 303 configured for accommodating and connecting to a vacuum generating device (e.g., a pump or a syringe). Eye docking element 301 is formed at least in part from elastic material, such as silicone rubber, and is configured to compress against outer surface of an eye while reducing the internal volume entrapped between an inner surface 304 thereof and the eye outer surface, when subjected to vacuum force via second port 303.

Figure 14A:
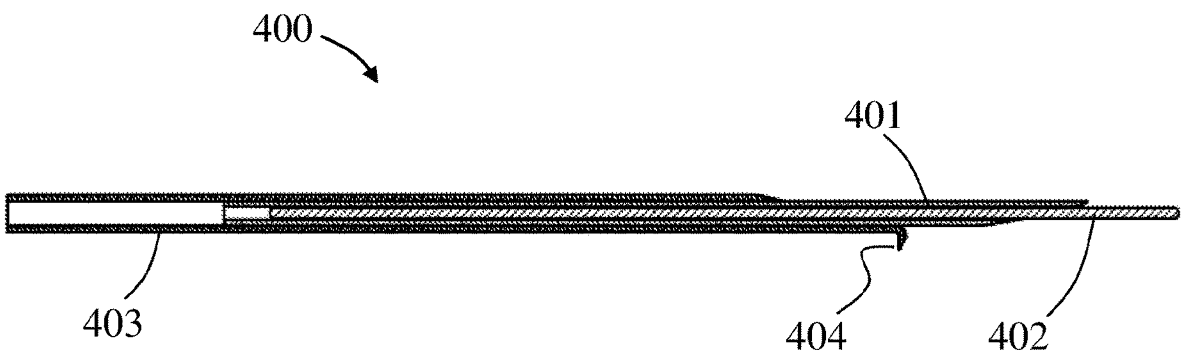
FIG. 14A illustrates a side cut view of an exemplary organ affecting device employing an organ docking hook, according to some embodiments of the invention.

FIG. 14A illustrates a side cut view of an exemplary organ affecting device 400 which is optionally an exemplary variation of system 11. Organ affecting device 400 includes a needle 401 (which may be similar in function and/or structure to needle 105), a tissue separator 402 (which may similar in function and/or structure to tissue separator 103) sized to slide in a lumen of needle 401, and an outer tube 403 sized to fit over and accommodate sliding of needle 401 through a lumen thereof. Outer tube 403 includes a hook 404 emerging from a distal tip thereof in an angle (optionally perpendicularly) to long axis of outer tube 403. Hook 404 is configured with a sharp tip for penetrating into and fixating to a soft tissue such as the sclera of the eye. Inner lumen of outer tube 403 can optionally be used for delivering fluid (medication) to lumen of needle 401, optionally around tissue separator 402, or optionally after its removal from needle 401.

Figure 14B:
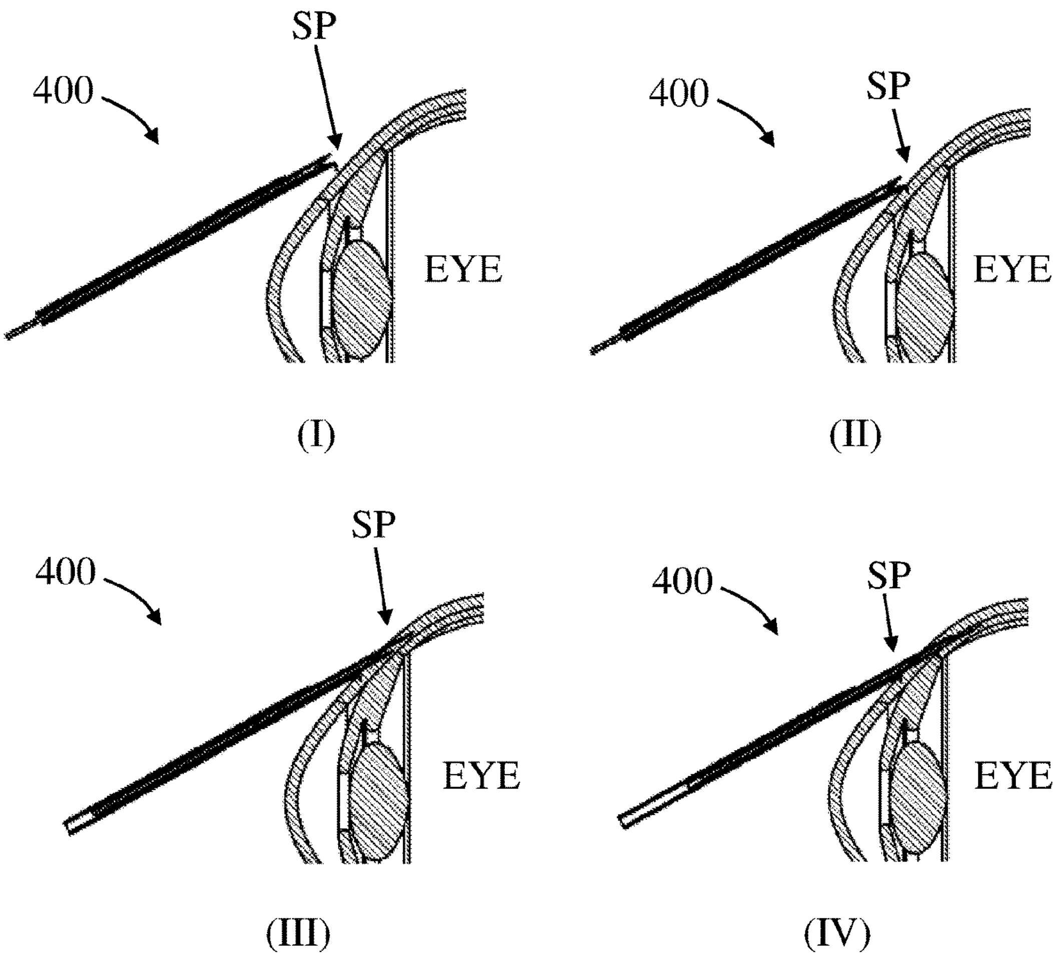
FIG. 14B illustrates views of the exemplary device shown in FIG. 14A in different configurations representing exemplary steps in a method for fixating a sclera portion, directing needle penetration into the sclera portion, and facilitating fluid injection to an interlayer region in an eye of a subject, according to some embodiments of the invention.

FIG. 14B illustrates views of the organ affecting device 400 in different configurations representing exemplary steps in a method for fixating a sclera portion SP, directing needle penetration into sclera portion SP, and facilitating fluid injection to an interlayer region in an eye of a subject. In Configuration (I), device 400 is positioned with hook 404 adjacent to target sclera portion SP, while distal tip of tissue separator 402 is provided proximally to distal tip of needle 401. In Configuration (II) hook 404 is partially penetrated into sclera portion SP following pressing of device 400 against sclera portion SP. In Configuration (III), while hook 404 fixates the eye via the anchored sclera portion SP by applying counter forces to prevent eyeball movement, needle 401 shown after being pushed forward and penetrating the sclera portion SP with distal tip thereof about 1 mm to 2 mm deep at a shallow angle relative to the outer surface of the eye (such that when needle 401 advances in the sclera, it does not pass through the sclera portion SP into the choroid layer). In Configuration (IV), while hook 404 fixates the eye and the needle 401 is positioned in place following its advancement into the sclera, tissue separator 402 is shown after having been pushed forward and penetrated across the sclera portion SP into the choroid layer with distal tip thereof about 2 mm to 3 mm deep relative to distal tip of needle 401. Tissue separator 402 may then be withdrawn, leaving an elongated passage (similar to passage SPG of FIG. 12N, for example) ready for delivery of medication.

Figure 15A:
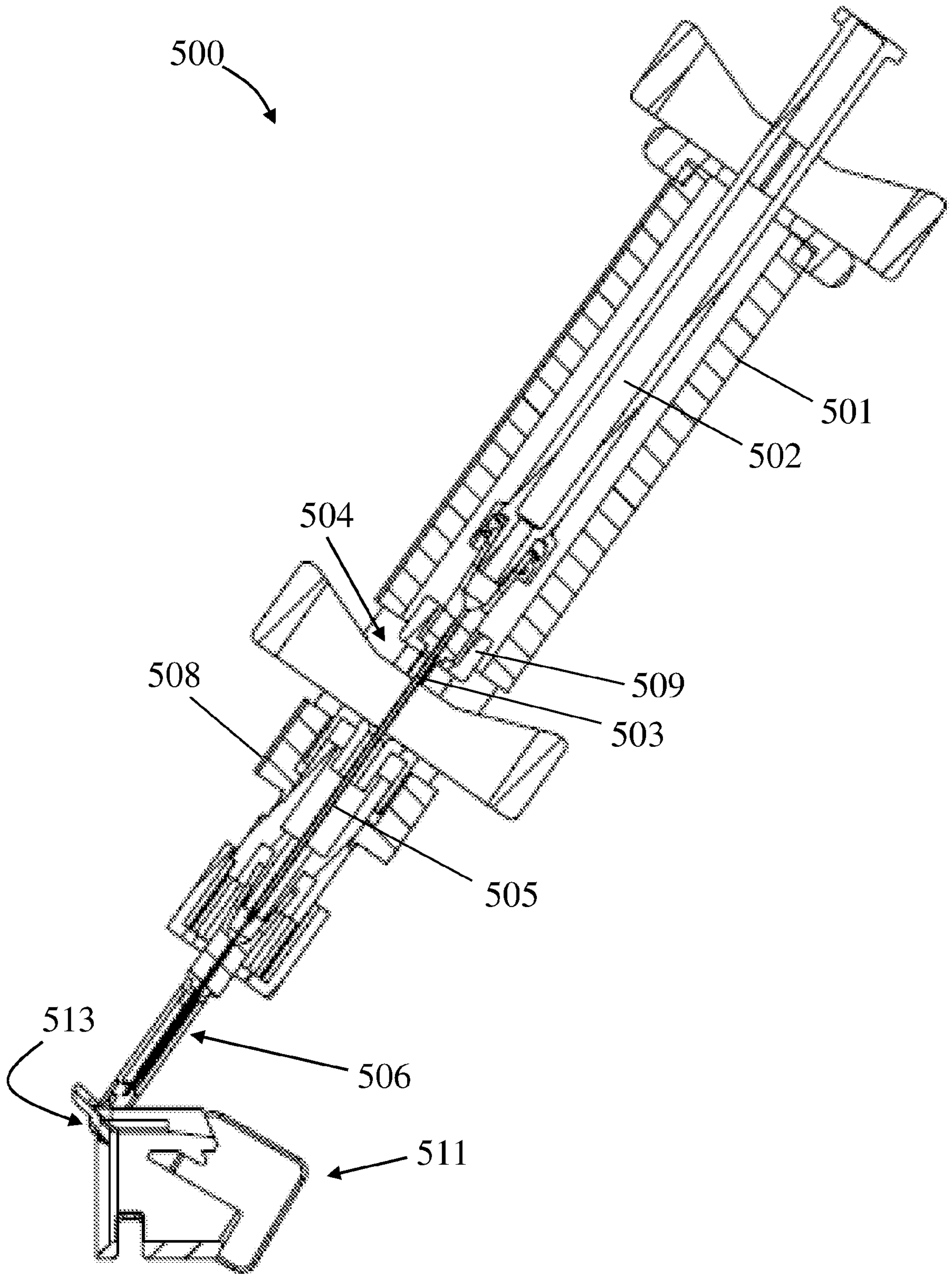
FIG. 15A illustrates a side cut view of an exemplary system unit for facilitating injections to an interlayer region in eye of a subject, according to some embodiments of the invention.

Reference is now made to FIG. 15A which illustrates a side cut view and rear view of an exemplary system unit 500 configured for facilitating injection into an interlayer region in the eye of a subject. System unit 500 includes a unit body 501 housing an elongated channel 502 configured for accommodating a length of a piston of a syringe for pressurizing a fluid therethrough. Elongated channel 502 is fluidly connected via a distal end thereof, within unit body 501, with a cannula 503 of a tissue separator 504 (being similar in function and structure to tissue separator 103). Tissue separator 504 further includes a slender probe 505 configured for fitting and sliding along a lumen of a needle 506 (being similar in function and structure to needle 105).

Figure 15B:
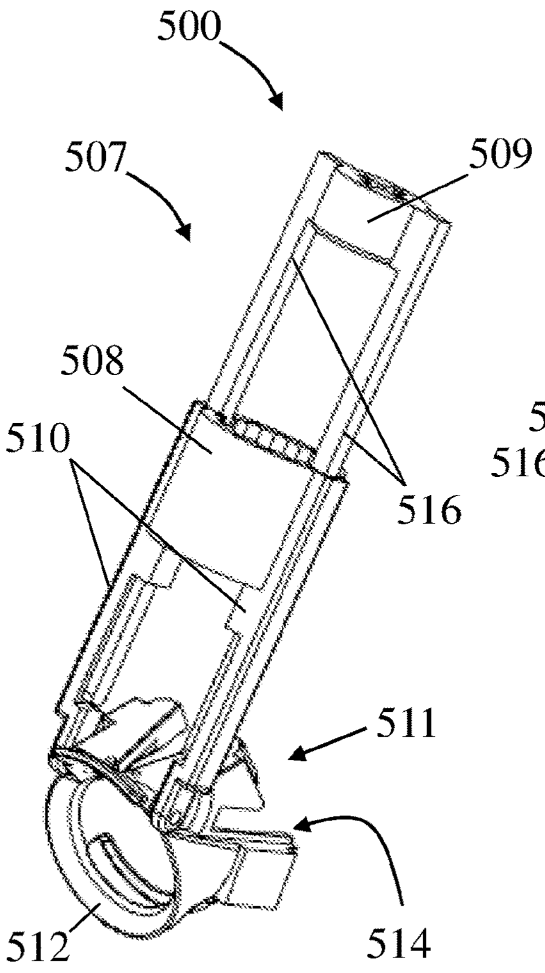
FIG. 15B illustrates an isometric view of exemplary components of the exemplary system unit shown in FIG. 15A, according to some embodiments of the invention.
Figure 15C:
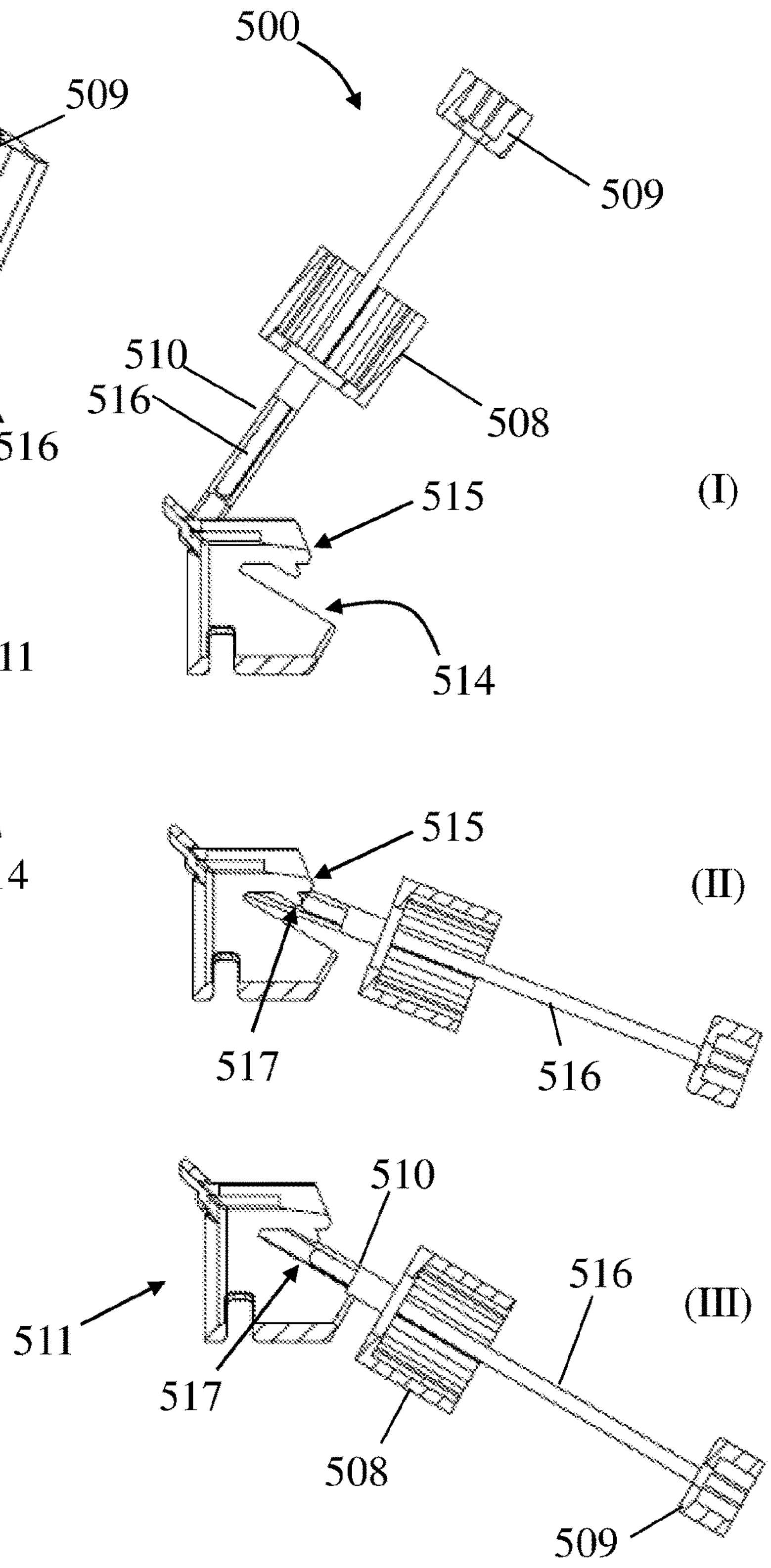
FIG. 15C illustrates views of the exemplary components shown in FIG. 15C in different configurations, according to some embodiments of the invention.

FIG. 15B illustrates an isometric view of some of the assembled components of system unit 500 (while illustratively concealing other components assembled in system unit 500, for sake of simplicity) and FIG. 15C illustrates views of the same assembled components in different configurations (I), (II) and (III). As shown, a retractable drawer mechanism 507, comprising a distal outer drawer 508 slidably connected to needle 506 and a proximal inner drawer 509 fixedly connected to tissue separator 504, is provided in unit body 501 and configured for facilitating (e.g., by confining or marking, for example) relative movement between tissue separator 504 and needle 506 to axial sliding of probe 505 in and through needle 506.

In Configuration (I), shown in FIG. 15C, unit body 501 with needle 506 is oriented at a steep penetration angle into target sclera portion of the eye within a range of 30° to 120°, optionally perpendicularly, relative to eye outer surface adjacent to needle penetration point (similarly to as shown in FIGS. 12F and 12G). In this configuration, tissue separator 504 can slide freely within needle 506.

In Configuration (II), shown in FIG. 15C, unit body 501 with needle 506 is oriented at an intermediate angle within a range of 10° to 30° s, relative to the eye outer surface adjacent to the penetration point. In this configuration, tissue separator is confined to a withdrawn position relative to distal tip of needle 506 and is entirely concealed in the needle lumen.

In Configuration (III), shown in FIG. 15C, unit body 501 with needle 506 is oriented at a shallow injection angle within a range of 0° to 10°, optionally tangentially, relative to the eye outer surface adjacent to the penetration point (similarly to as shown in FIG. 12K). In this configuration, tissue separator 504 can slide freely within needle 506.

Distal outer drawer 508 connects with outer arms 510 thereof unit body 501 to an organ docking member 511 by way of pivot connection, thereby facilitating a range of angular orientations of needle 506 relative to an organ contact surface 512 provided at a distal end of organ docking member 511 and configured to fit or conform to a shape imposed by outer surface of a target organ (e.g., eyeball). Organ docking member 511 is similar in function and structure to organ docking device 200 and further includes anchors 513 for fixating a target tissue portion, prior to needle 506 penetration therethrough, and needle directing surfaces 514 configured to facilitate a predetermined needle penetration path across organ contact surface 512 when outer arms 510 rest thereon and needle 506 travels distally towards organ contact surface 512.

Organ docking member 511 further includes curved track surfaces 515 configured to effect linear motion of tissue separator 504 relative to needle 506 during rotation of outer arms 510 from a far position relative to needle directing surfaces 514 (as shown in Configuration (I) in FIG. 15C, for example) to near position relative to needle directing surfaces 514 (as shown in Configuration (II) in FIG. 15C, for example). Proximal inner drawer 509 includes inner arms 516 each having track follower surface 517 configured and arranged for continuous sliding on a respective curved track surface 515 during outer arms 510 rotation from the far position to the near position, such that tissue separator 504 is withdrawn during outer arms 510 motion from an intermediate position (e.g., similar to intermediate position shown in FIG. 8A) to a withdrawn position (e.g., similar to proximal-most position shown in FIG. 8B).

This motion of tissue separator 504 relative to needle 506 is considered advantageous as it effects a precise shift along a very short travel (e.g., 1 mm or less, optionally about 0.5 mm) during unit body 501 rotation and allows the user to concentrate on other aspects of the process in this delicate maneuver.

Each of the following terms written in singular grammatical form: ‘a’, ‘an’, and ‘the’, as used herein, means ‘at least one’, or ‘one or more’. Use of the phrase ‘one or more’ herein does not alter this intended meaning of ‘a’, ‘an’, or ‘the’. Accordingly, the terms ‘a’, ‘an’, and ‘the’, as used herein, may also refer to, and encompass, a plurality of the stated entity or object, unless otherwise specifically defined or stated herein, or, unless the context clearly dictates otherwise. For example, the phrases: ‘a unit’, ‘a device’, ‘an assembly’, ‘a mechanism’, ‘a component’, ‘an element’, and ‘a step or procedure’, as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: ‘includes’, ‘including’, ‘has’, ‘having’, ‘comprises’, and ‘comprising’, and, their linguistic/grammatical variants, derivatives, or/and conjugates, as used herein, means ‘including, but not limited to’, and is to be taken as specifying the stated component(s), feature(s), characteristic(s), parameter(s), integer(s), or step (s), and does not preclude addition of one or more additional component(s), feature(s), characteristic(s), parameter(s), integer(s), step(s), or groups thereof. Each of these terms is considered equivalent in meaning to the phrase ‘consisting essentially of’.

The term ‘method’, as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as 'l', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably. For example, for stating or describing the numerical range of room temperature, the phrase 'room temperature refers to a temperature in a range of between about 20° C. and about 25° C.', and is considered equivalent to, and meaning the same as, the phrase 'room temperature refers to a temperature in a range of from about 20° C. to about 25° C.'.

The term 'about', as used herein, refers to +10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment, may also be illustratively described and presented in the context or format of a plurality of separate embodiments.

Although the invention has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

All publications, patents, and or/and patent applications, cited or referred to in this disclosure are herein incorporated in their entirety by reference into the specification, to the same extent as if each individual publication, patent, or/and patent application, was specifically and individually indicated to be incorporated herein by reference. In addition, citation or identification of any reference in this specification shall not be construed or understood as an admission that such reference represents or corresponds to prior art of the present invention. To the extent that section headings are used, they should not be construed as necessarily limiting.

What is claimed is:

1. A device for injection into an interlayer of an organ of a subject, the device comprising:

- a needle comprising a needle lumen extending between a needle proximal end and a needle distal end, said needle distal end including a size transitional portion terminating in a sharp needle distal tip;
- an elongated tissue separator having a separator distal tip, at least a portion of said elongated tissue separator being shiftable in the needle lumen; and
- an actuator configured to shift said elongated tissue separator in said needle lumen between a first position, wherein said separator distal tip is fixedly positioned proximally to said needle distal tip, and a second position, wherein said separator distal tip is fixedly positioned a first predetermined distance distally from said needle distal tip; and
- a cannula fluidly connectable between a syringe and said needle lumen, so that a fluid injected from said syringe is directly flowable to said needle distal tip via said cannula and said needle lumen.

2. The device according to claim 1, wherein when said separator distal tip is in said first position, said separator distal tip protrudes from a laterally uncovered section of said size transitional portion.

3. The device according to claim 1, wherein said elongated tissue separator has any one or more of the following features:

- a. said elongated tissue separator includes said cannula and an elongated probe comprising a probe fixed portion connected to an inner cannula wall of said cannula and a probe protruding portion extending distally from a cannula distal end of said cannula and terminating in said separator distal tip;
- b. said elongated tissue separator is configured to allow flow of a fluid from said cannula to said needle lumen around said probe fixed portion;
- c. the cannula is provided with a seal configured to allow sliding of said elongated tissue separator therealong;
- d. the cannula is provided with said seal configured to allow sliding of said elongated tissue separator therealong and said cannula distal end is positioned within or distally to, said seal when said separator distal tip is fixedly positioned proximally to said needle distal tip and fixedly positioned the first predetermined distance distally from said needle distal tip.

4. The device according to claim 1, wherein said syringe is connectable to a separator hub of said elongated tissue separator.

5. The device according to claim 1, further comprising an external stopper provided externally to said needle and configured to prevent penetration of said needle distal tip in the organ beyond a second predetermined distance.

6. The device according to claim 5, wherein said external stopper has any one or more of the following features:

- a. said external stopper is a tube extending along said needle with a stopper distal end thereof located proximally to said needle distal tip by said second predetermined distance; and
- b. said external stopper is a tube extending along said needle with said stopper distal end thereof located proximally to said needle distal tip by said second predetermined distance and said stopper distal end is fixedly positioned, or selectively shiftable along said needle, proximally to said size transitional portion.

7. The device according to claim 1, wherein said actuator comprises a switch, the switch being switchable between two or more switch modes for shifting the actuator between fixed positions of the actuator.

8. The device according to claim 1 further comprising an organ docking device for fixating a target tissue portion of the organ and directing needle penetration into the target tissue portion, the organ docking device comprising:

- an organ docking device body comprising an organ contact surface, configured to conform to a surface of the target tissue portion, and a needle directing surface configured to guide the needle in a penetration path through said organ contact surface;
- an anchoring member configured to anchor the organ docking device to said target tissue portion; and an anchoring actuator configured to shift said anchoring member between a withdrawn position, wherein said anchoring member is prevented from physically interacting with the target tissue portion when in contact with said organ contact surface, and an anchoring position, wherein said anchoring member anchors to said target tissue portion so as to generate counteracting forces between said organ docking device body and the organ during penetration into the target tissue portion with said needle along said penetration path.

9. The device according to claim 8, wherein said anchoring member has any one or more of the following properties:

a. said anchoring member comprises at least one anchor connected to said organ docking device body, the at least one anchor being provided with a sharp anchor tip for penetrating into said target tissue portion;

b. when the anchoring member is in said withdrawn position, said anchor tip is positioned proximally to said organ contact surface, and when the anchoring member is in said anchoring position, said anchor tip is positioned distally to said organ contact surface for anchoring to the target tissue portion; and c. when the anchoring member is in said anchoring position, said at least one anchor is directed from a peripheral point towards an opposing peripheral point, around said organ contact surface.

10. The device according to claim 8, further comprising a tissue pressing member configured for pressing against said target tissue portion when in contact with said organ contact surface.

11. The device according to claim 8, wherein said needle directing surface is tiltable relative to the organ docking device.

12. The device according to claim 8, wherein said anchoring member includes a first anchor and a second anchor.

13. The device according to claim 12, wherein said needle-penetration path passes between said first anchor and said second anchors.

14. The device according to claim 12, wherein each one of said first anchor and said second anchor includes an anchor size transitional portion ending with said an anchor distal tip and a slender restrictor with a blunt restrictor tip thereof fixedly positioned between ends of said anchor size transitional portion and is protruding from a laterally uncovered section of said anchor size transitional portion.

15. The device according to claim 8, wherein said anchoring actuator comprises an anchoring trigger configured to cause at least one anchor to shift between said withdrawn position and said anchoring position.

16. The device according to claim 1, wherein the interlayer of the organ of the subject comprises a suprachoroidal space of an eye of the subject, and said fluid comprises a therapeutic composition comprising viscous agents for a short term buckling effect or a long term buckling effect.

17. A method for injection of a substance or object into an interlayer region in an eye of a subject, the method comprising:

a. providing a device for injection into an interlayer of an organ of the subject, the device comprising:

a needle comprising a needle lumen extending between a needle proximal end and a needle distal end, said needle distal end including a size transitional portion terminating in a sharp needle distal tip;

an elongated tissue separator having a separator distal tip, at least a portion of said elongated tissue separator being shiftable in the needle lumen; and an actuator configured to shift said elongated tissue separator in said needle lumen between a first position, wherein said separator distal tip is fixedly positioned proximally to said needle distal tip, and a second position, wherein said separator distal tip is fixedly positioned a first predetermined distance distally from said needle distal tip;

b. positioning said separator distal tip at the first position between ends of said size transitional portion, c. positioning said separator distal tip at a first predetermined distance proximally to said needle distal tip, the separator distal tip protruding from the size transitional portion;

d. penetrating an outer surface of the organ at a penetration point into the organ using said needle distal tip until contacting an organ outer surface layer with said separator distal tip, wherein said first predetermined distance distally from said needle distal tip is shorter than a thickness of said organ outer surface layer adjacent to said penetration point; and e. injecting said substance or object into the interlayer of the organ.

18. The method according to claim 17 further comprising using said actuator to shift said elongated tissue separator longitudinally in said needle lumen such that said separator distal tip is repositioned to a distal-most position, wherein said separator distal tip is located a second predetermined distance distally to said needle distal tip, thereby advancing in said organ outer surface layer and penetrating through said organ outer surface layer into the interlayer of the organ and forming a passage in said interlayer of the organ with said separator distal tip.

19. The method according to claim 17, comprising creating a directional space in the interlayer region, and filling the directional space with fluid which then disperses throughout the interlayer region.

* * * * *